United States Patent
Holm

(10) Patent No.: US 9,439,809 B2
(45) Date of Patent: Sep. 13, 2016

(54) METHOD OF STERILIZATION OF WOUND DRESSINGS

(75) Inventor: David R. Holm, Hudson, WI (US)

(73) Assignee: 3M Innovative Properties Company, St. Paul, MN (US)

(*) Notice: Subject to any disclaimer, the term of this patent is extended or adjusted under 35 U.S.C. 154(b) by 268 days.

(21) Appl. No.: 13/635,536

(22) PCT Filed: Mar. 16, 2011

(86) PCT No.: PCT/US2011/028660
§ 371 (c)(1),
(2), (4) Date: Sep. 17, 2012

(87) PCT Pub. No.: WO2011/119393
PCT Pub. Date: Sep. 29, 2011

(65) Prior Publication Data
US 2013/0011296 A1 Jan. 10, 2013

Related U.S. Application Data

(60) Provisional application No. 61/317,757, filed on Mar. 26, 2010.

(51) Int. Cl.
| | |
|---|---|
| *A61L 2/00* | (2006.01) |
| *A61F 13/00* | (2006.01) |
| *C08J 3/28* | (2006.01) |
| *C08J 7/02* | (2006.01) |
| *A61L 2/08* | (2006.01) |

(52) U.S. Cl.
CPC ... *A61F 13/00991* (2013.01); *A61F 13/00042* (2013.01); *C08J 3/28* (2013.01); *C08J 7/02* (2013.01); *A61F 2013/00314* (2013.01); *A61F 2013/00748* (2013.01); *A61L 2/087* (2013.01); *C08J 2353/02* (2013.01)

(58) Field of Classification Search
CPC .................. A61L 2/087; A61L 15/60; A61F 2013/00748
USPC .......................................................... 422/22
See application file for complete search history.

(56) References Cited

U.S. PATENT DOCUMENTS

| | | | |
|---|---|---|---|
| 3,779,706 A | 12/1973 | Nablo | |
| 3,841,953 A | 10/1974 | Lohkamp | |
| 5,176,952 A | 1/1993 | Joseph | |
| 5,409,472 A | 4/1995 | Rawlings | |
| 5,437,932 A | 8/1995 | Ali | |
| 5,989,498 A | 11/1999 | Odland | |
| 6,039,940 A | 3/2000 | Perrault | |
| 6,040,493 A * | 3/2000 | Cooke et al. | 602/41 |
| 6,075,177 A * | 6/2000 | Bahia et al. | 602/43 |
| 6,203,755 B1 | 3/2001 | Odland | |
| 6,548,727 B1 | 4/2003 | Swenson | |
| 6,698,162 B2 * | 3/2004 | Shudo et al. | 53/428 |
| 6,706,684 B1 | 3/2004 | Bayon | |
| 7,264,772 B2 | 9/2007 | Ashby | |
| 2002/0005028 A1 | 1/2002 | Shudo | |
| 2003/0203013 A1 * | 10/2003 | Serafica et al. | 424/445 |
| 2004/0180093 A1 | 9/2004 | Burton | |
| 2004/0241246 A1 | 12/2004 | Lipman | |
| 2005/0012350 A1 | 1/2005 | Kelsey | |
| 2005/0123590 A1 | 6/2005 | Burton | |
| 2005/0124724 A1 | 6/2005 | Burton | |
| 2006/0085080 A1 * | 4/2006 | Bechgaard | A61F 2/30721 623/23.43 |
| 2006/0173087 A1 * | 8/2006 | Hyde | A61L 15/225 521/82 |
| 2008/0125513 A1 | 5/2008 | Kristiansen | |
| 2009/0246238 A1 * | 10/2009 | Gorman et al. | 424/402 |
| 2012/0083723 A1 | 4/2012 | Vitaris | |

FOREIGN PATENT DOCUMENTS

| | | |
|---|---|---|
| EP | 0126528 | 11/1988 |
| EP | 0172724 | 7/1991 |
| EP | 0489967 | 6/1992 |
| WO | WO 96-25469 | 8/1996 |
| WO | WO 97-23577 | 7/1997 |
| WO | WO 02-066087 | 8/2002 |
| WO | WO 2009-132229 | 10/2009 |

OTHER PUBLICATIONS

Calvert, Chapter II—The Interaction of Light with Atoms; Atom-Photosensitized Reactions, Photochemistry, 27-117 (1966).
Hangeman, "Photoinitiators for Free Radical Polymerization" Progress in Organic Coatings, Mar. 1985, vol. 13, No. 2, pp. 123-150.
Rehim, "Swelling of radiation crosslinked acrylamide-based microgels and their potential applications", Radiation Physics and Chemistry, Oct. 2005, vol. 74, No. 2, pp. 111-117.
Rosiak, "Synthesis of hydrogels by irradiation of polymers in aqueous solution", Radiation Physics and Chemistry, Jun. 1999, vol. 55, No. 2, pp. 139-151.
Wente, "Manufacture of Superfine Organic Fibers," Naval Rersearch Laboratories Report No. 4364, May 25, 1954, 19 pages.
Wente, "Superfine Thermoplastic Fibers", Naval Research Laboratory, Industrial and Engineering Chemistry, Aug. 1956, vol. 48, No. 8, pp. 1342-1346.
International Search Report for PCT International Application No. PCT/US2011/028660, Mailed Nov. 24, 2011, 3 pages.

* cited by examiner

*Primary Examiner* — Kevin Joyner
(74) *Attorney, Agent, or Firm* — Jeffrey M. Olofson

(57) ABSTRACT

Methods of sterilizing articles such as wound dressings, include the steps of providing an article that includes a polymer layer, applying an aqueous solution to the polymer layer and applying electron beam radiation to the article. The polymer layer includes a hydrophobic organic matrix that includes an elastomeric polymer and hydrophilic polymeric microparticles dispersed within the elastomeric polymer. Applying the aqueous solution to the polymer layer at least partially swells the hydrophilic microparticles of the polymer layer. In some articles the polymer layer includes an elastomeric polymer, hydrophilic polymeric microparticles dispersed within the elastomeric polymer, and hydrophilic polymer particles with greater than 10 micrometers average particle size dispersed within the hydrophobic organic matrix. These articles may be sterilized by applying either electron beam or gamma radiation.

20 Claims, No Drawings

METHOD OF STERILIZATION OF WOUND DRESSINGS

CROSS REFERENCE TO RELATED APPLICATIONS

This application is a national stage filing under 35 U.S.C. 371 of PCT/US2011/028660, filed Mar. 16, 2011, which claims priority to U.S. Provisional Patent Application No. 61/317,757, filed Mar. 26, 2010, the disclosure of which is incorporated by reference in its/their entirety herein.

FIELD OF THE DISCLOSURE

This disclosure deals generally with wound dressings and methods for sterilizing wound dressings.

BACKGROUND

A variety of wound dressings are used to treat a variety of wounds. Generally these wound dressings are preferably designed so as not to stick to the wound bed. Also, it is desirable if they are pliable and have a soft wound-contacting surface. In addition, it is desirable if they are capable of donating some moisture to a dry wound and also absorbing excess amounts of wound exudate and/or to allow for the passage of wound exudate into an absorbent material placed over the dressing.

The sterilization of wound dressings prior to use on a patient is important to ensure the safety of the patient. Typical methods used to sterilize wound dressings are ethylene oxide gas sterilization, gas plasma technology, steam sterilization, gamma irradiation, and electron beam irradiation. Each sterilization method has advantages and disadvantages in terms of types of packaging needed, cost and impact on the properties of the dressing throughout its shelf life. Ethylene oxide and gas plasma sterilization methods require a gas to permeate into the packaged product and come into contact with the surface of the dressing to reduce the bioburden of the dressing. This requirement to penetrate the packaging material in order to ensure sterility limits the type of packaging that can be used (i.e., the packaging must be permeable to the sterilizing gas). Dressings that contain significant levels of moisture are typically not sterilized using these gas sterilization methods because moisture would most likely also be transported through the permeable packaging, thereby limiting the shelf life of the product. Steam sterilization, gamma irradiation, and electron beam irradiation can be applied to wider range of packaging systems, but these methods also have disadvantages. Steam sterilization can be problematic, because the application of heat to the dressing can adversely affect the dressing. Similarly, application of gamma or electron beam radiation to a dressing, especially a polymeric based dressing, can cause crosslinking or degradation of the polymer to occur in the polymer, thus changing the properties of the dressing.

SUMMARY

The polymer compositions of the present disclosure can be used in wound dressings, i.e., medical articles that are applied directly to a wound or used to treat a wound. Such articles include a backing (i.e., a support substrate) that is porous. The composition of the present disclosure can be used by itself or in combination with a support substrate on which the composition may be coated or into which the composition may be impregnated.

Disclosed herein are methods of sterilizing articles comprising providing an article, wherein the article comprises a polymer layer, applying an aqueous solution to the polymer layer and applying electron beam radiation to the article. The polymer layer comprises a hydrophobic organic matrix comprising an elastomeric polymer, and hydrophilic polymeric microparticles dispersed within the elastomeric polymer. Applying an aqueous solution to the polymer layer at least partially swells the hydrophilic microparticles of the polymer layer. In some embodiments, the article is placed into a non-porous package after applying an aqueous solution and prior to applying electron beam radiation.

Also disclosed are methods of sterilizing articles comprising providing an article, wherein the article comprises a polymer layer, applying an aqueous solution to the polymer layer and applying gamma radiation to the article. The polymer layer comprises a hydrophobic organic matrix comprising an elastomeric polymer, with hydrophilic polymeric microparticles dispersed within the elastomeric polymer and hydrophilic polymer particles with greater than 10 micrometers average particle size dispersed within the hydrophobic organic matrix. The aqueous solution is applied to the polymer layer such that the ratio of water to hydrophilic polymeric microparticles is in the range of 0.2:1 to 6:1, and the aqueous solution at least partially swells the hydrophilic microparticles of the polymer layer. In some embodiments, the article is placed into a non-porous package after applying an aqueous solution and prior to applying gamma radiation.

DETAILED DESCRIPTION

The need remains for methods to sterilize wound dressings, especially wound dressings that contain water, such as hydrogels. Hydrogel dressings are particularly desirable wound dressings because they are soft and pliable, do not adhere to the wound, can donate moisture to a dry wound, and also may have absorbent properties. However, hydrogel dressings are typically supplied in a non-porous package system for the prevention of moisture loss prior to use and therefore are not efficiently sterilized by gas permeation techniques. Also, they can be thermally and radiation sensitive and therefore steam sterilization, gamma irradiation, and electron beam irradiation can also be problematic for these dressings. Exposure of hydrogel dressings that contain moisture can be particularly problematic. As described in the journal article: Physics and Chemistry 74 (2005) 111-117 "Swelling of radiation crosslinked acrylamide-based microgels and their potential applications", in the presence of moisture, electron beam radiation causes a higher level of further crosslinking (compared to no moisture present) and as a consequence there has a lower swell ratio or water uptake. Contrary to this teaching, the wound dressings of this disclosure, even with water present in the hydrogel layer, retain much of their moisture absorbency even after exposure to electron beam or gamma radiation.

In this disclosure, methods of sterilization of hydrogel wound dressings are presented that include the preparation of a wound dressing containing a polymer layer, the application of water to this polymer layer to form a hydrogel layer, and the irradiation of the hydrogel wound dressing with electron beam radiation, or in some embodiments with gamma radiation. In some embodiments, the hydrogel wound dressing is placed in a package prior to irradiation. The radiation does not substantially adversely affect the absorptive properties or moisture holding capacity of the hydrogel wound dressing. In other words, the absorptivity of the hydrogel layer after irradiation is at least 40% or more of the absorptivity of the hydrogel layer prior to irradiation. In some embodiments, the absorptivity is 60% or more or even 80% or more of the absorptivity of the hydrogel layer prior to irradiation.

The wound dressing comprises a polymer layer, water and may optionally include a porous web. The porous web can provide support and strengthening to the polymer layer that contains water. The wound dressing may also optionally include one or more liners to cover and protect the dressing surface until the dressing is to be used. The polymer layer comprises a hydrophobic organic matrix with hydrophilic microparticles dispersed within the hydrophobic organic matrix. The hydrogel layer may also optionally include additional hydrophilic particles which are greater than 10 micrometers in average unswollen diameter. The hydrophobic organic matrix comprises at least one elastomeric polymer, an optional plasticizing agent as well as other optional additives such as tackifying agents.

As used herein, "a," "an," "the," "at least one," and "one or more" are used interchangeably. Also herein, the recitations of numerical ranges by endpoints include all numbers subsumed within that range (e.g., 1 to 5 includes 1, 1.5, 2, 2.75, 3, 3.80, 4, 5, etc.).

The terms "polymer" and "polymeric material" refer to macromolecular materials prepared from one monomer such as a homopolymer or to materials prepared from two or more monomers such as a copolymer, terpolymer, or the like. The term "polymer layer" refers to a layer that contains at least one polymeric material and may contain a blend of different polymeric materials as well as additional components.

Hydrogels, also called aquagels, are networks of polymer chains that are water-insoluble, and can be highly absorbent, and also possess a degree of flexibility due to their significant water content. As used herein, the term "hydrogel" refers to a composition containing a hydrophobic organic matrix with hydrophilic microparticles dispersed within the hydrophobic organic matrix, with at least some water contained in the hydrophilic microparticles. Typically, the hydrophobic organic matrix forms a continuous matrix with the hydrophilic microparticles substantially uniformly dispersed therein. The term "polymer layer" is used herein to describe the composition prior to application of water and the term "hydrogel" is used to describe the composition after the application of water.

In the context of the hydrogels of this disclosure, the term "absorbent" means that the composition demonstrates a saline (i.e. 0.9% NaCl solution) absorbency that is at least 50% of the dry weight of the hydrogel composition.

As used herein, the term "microparticles" refers to particles with an average diameter of less than 10 micrometers. Unless otherwise specified, in the case of hydrophilic microparticles or particles, the average diameter refers to the average diameter in the unswollen or dry state.

As used herein, "hydrophobic" when referring to, for example, a polymer matrix, means that the polymeric matrix is antagonistic to, sheds, tends not to combine with, or is incapable of dissolving in water. Typically, hydrophobic matrices absorb less that 10% of their dry weight in water, often much less than 10% by weight.

As used herein, "hydrophilic" when referring to, for example, microparticles, means that the microparticles have an affinity for water and aqueous solutions, and readily absorb water or aqueous solutions.

As used herein, "aqueous solution", refers to a liquid composition comprising at least water, and may also contain additional components dissolved in or miscible with water.

The term "adhesive" as used herein refers to polymeric compositions useful to adhere together two adherends. Examples of adhesives are heat activated adhesives and pressure sensitive adhesives.

Heat activated adhesives are non-tacky at room temperature but become tacky and capable of bonding to a substrate at elevated temperatures. These adhesives usually have a Tg or melting point (Tm) above room temperature. When the temperature is elevated above the Tg or Tm, the storage modulus usually decreases and the adhesive becomes tacky.

Pressure sensitive adhesive compositions are well known to those of ordinary skill in the art to possess properties including the following: (1) aggressive and permanent tack, (2) adherence with no more than finger pressure, (3) sufficient ability to hold onto an adherend, and (4) sufficient cohesive strength to be cleanly removable from the adherend. Materials that have been found to function well as pressure sensitive adhesives are polymers designed and formulated to exhibit the requisite viscoelastic properties resulting in a desired balance of tack, peel adhesion, and shear holding power. Obtaining the proper balance of properties is not a simple process.

The wound dressings of this disclosure comprise a hydrogel layer. The hydrogel layer includes a hydrophobic organic matrix. The hydrophobic organic matrix comprises at least one elastomeric polymer. A wide variety of elastomeric polymers are suitable, including polymers which by themselves can be classified as adhesive polymers, including pressure sensitive adhesives. Adhesive polymers are suitable as the hydrophobic organic matrix, despite the fact that it is desirable for the hydrogel layer to not have adhesive properties. The hydrogel layer, because of the presence of the other components besides the hydrophobic organic matrix, such as water, may not have adhesive properties.

Examples of elastomeric polymers include, but are not limited to, polyisobutylene, polyethylene-propylene rubber, polyethylene-propylene diene-modified rubber, polyisoprene, styrene-isoprene-styrene, styrene-butadiene-styrene, styrene-ethylene-propylene-styrene, and styrene-ethylene-butylene-styrene. Particularly desirable elastomeric polymers include styrene block copolymers such as styrene-isoprene-styrene copolymers, styrene-butadiene-styrene copolymers, and styrene-ethylene-butylene-styrene copolymers. In some embodiments, styrene-ethylene-butylene-styrene copolymers are particularly desirable, such as, for example the polymer KRATON G4609H commercially available from Kraton Polymers, Houston, Tex.

Other polymers (referred to herein as "optional secondary polymers") may also be included within the hydrophobic polymer matrix. The following are examples of such polymers.

Elastomeric polymers useful as optional secondary polymers are typically materials that form one phase at 21° C., have a glass transition temperature less than 0° C., and exhibit elastomeric properties. The elastomeric polymers include, but are not limited to, polyisoprenes, styrene-diene block copolymers, natural rubber, polyurethanes, polyether-block-amides, poly-alpha-olefins, (C1-C20) acrylic esters of meth(acrylic) acid, ethylene-octene copolymers, and combinations thereof. Useful elastomeric materials include, for example, natural rubbers such as CV-60 (a controlled viscosity grade natural rubber having Mooney viscosity of 60+/−5 mL, 1+4 at 100° C., available as an International commodity); butyl rubbers, such as Exxon Butyl 268 available from Exxon Chemical Co., Houston, Tex.; synthetic poly-isoprenes such as CARIFLEX IR309, available from Kraton Polymers, Houston, Tex., and NATSYN 2210, available from Goodyear Tire and Rubber Co., Akron, Ohio; ethylene-propylenes; polybutadienes; polyisobutylenes such as VISTANEX MM L-80, available from ExxonMobil Chemical Co.; and styrene-butadiene random copolymer rubbers such as AMERIPOL 1011A, available from BF Goodrich of Akron, Ohio.

Thermoplastic polymers useful as optional secondary polymers include, for example, polyolefins such as isotactic polypropylene; low density or linear low density polyethylene; medium density polyethylene; high density polyethylene; polybutylene; polyolefin copolymers or terpolymers, such as ethylene/propylene copolymer and blends thereof; ethylene-vinyl acetate copolymers such as ELVAX 260, available from E.I. DuPont de Nemours & Co., Wilmington, Del.; ethylene acrylic acid copolymers; ethylene methacrylic acid copolymers such as SURLYN 1702, available from E. I. DuPont de Nemours & Co.; polymethylmethacrylate; polystyrene; ethylene vinyl alcohol; polyester; amorphous polyester; polyamides; fluorinated thermoplastics such a polyvinylidene fluoride; polytetrafluoroethylene; fluorinated ethylene/propylene copolymers; halogenated thermoplastics such as a chlorinated polyethylene; and combinations thereof. Other exemplary thermoplastic polymers are disclosed in International Publication No. WO 97/23577. Generally, if used, the thermoplastic polymer is a polyolefin.

Thermoplastic elastomeric polymers useful as optional secondary polymers in this disclosure are typically materials that form at least two phases at 21° C., flow at a temperature greater than 50° C. and exhibit elastomeric properties. Useful thermoplastic elastomeric materials include, for example, linear, radial, star and tapered styrene-isoprene block copolymers such as KRATON D1107P, available from Kraton Polymers, and EUROPRENE SOL TE 9110, available from EniChem Elastomers Americas, Inc. Houston, Tex., linear styrene-(ethylene/butylene) block copolymers such as KRATON G1657 available from Kraton Polymers, linear styrene-(ethylene/propylene) block copolymers such as KRATON G1657X available from Kraton Polymers, styrene-isoprene-styrene block copolymers such as KRATON D1119P available from Kraton Polymers, linear, radial, and star styrene-butadiene block copolymers such as KRATON D1118X, available from Kraton Polymers, and EUROPRENE SOL TE 6205 available from EniChem Elastomers Americas, Inc., polyetheresters such as HYTREL G3548, available from E. I. DuPont de Nemours & Co., and poly-alpha-olefin based thermoplastic elastomeric materials such as those represented by the formula —($CH_2$—CHR) where R is an alkyl group containing 2 to 10 carbon atoms and poly-alpha-olefins based on metallocene catalysis such as ENGAGE EG8200, an ethylene/1-octene copolymer available from DuPont Dow Elastomers Co., Wilmington, Del. Other exemplary thermoplastic elastomers are disclosed in International Publication No. WO 96/25469.

The hydrophobic organic matrix may also comprise a pressure sensitive adhesive. Pressure sensitive adhesives useful in the present disclosure include natural rubbers, synthetic rubbers, styrene block copolymers, polyvinyl ethers, acrylics, poly-alpha-olefins, and silicones. The pressure sensitive adhesive may contain one or more polymeric materials as well as optional additives such as plasticizing agents or tackifying agents. Mixtures and blends or pressure sensitive adhesives may also be used.

Optional plasticizing agents (i.e., plasticizers) selected for use in the compositions of the present disclosure can possess a range of properties. Generally, the plasticizing agents can be liquid, semi-solid or solid, have a range of molecular weights and architectures (e.g., be monomeric or polymeric in nature), and are compatible with the other components of the polymer composition. Additionally, mixtures of solid and liquid, monomeric and polymeric and other combinations of plasticizing agents can be used.

For certain embodiments, elastomeric plasticizing agents can be used. Such plasticizing agents can be derived from low molecular weight naphthalenic oils, or low molecular weight acids, or alcohols, which are then esterified with respectively a monofunctional alcohol or monofunctional acid. Examples of these are mineral oil, cetostearyl alcohol, cetyl alcohol, cholesterol, coconut oil, oleyl alcohol, steryl alcohol, and squalane. Some elastomers are more compatible with esters of mono- and multibasic acids, such as isopropyl myristate, isopropyl palmitate, dibutyl phthalate, diisoctyl phthalate, dibutyl adipate, dibutyl sebacate, and the like. Useful polymeric plasticizing agents include non-acrylic plasticizing agents, which are typically derived from cationically or free-radically polymerizable monomers, condensation polymerizable monomers, or ring-opening polymerizable monomers to make low molecular weight polymers. Examples of these polymeric plasticizing agents include materials such as polyurethanes, polyureas, polyvinylethers, polyethers, polyesters, and the like.

Useful plasticizing agents are compatible with the elastomeric polymer or polymers, such that once the plasticizing agent is mixed therein, the formed hydrophobic organic matrix does not phase separate. By "phase separation" or "phase separate", it is meant that by differential scanning calorimetry (DSC) no detectable thermal transition, such as a melting or glass transition temperature can be found for the pure plasticizing agent in the plasticized composition. Some migration of the plasticizing agent from or throughout the plasticized composition can be tolerated, such as minor separation due to composition equilibrium or temperature influences, but the plasticizing agent does not migrate to the extent of phase separation between the polymer(s) of the hydrophobic polymer matrix and the plasticizing agent.

Generally, useful plasticizing agents are non-reactive, thus preventing copolymerization with any reactive groups on the elastomeric polymers or the hydrophilic microparticles. Thus, for example, plasticizing agents having acrylate functionality, methacrylate functionality, styrene functionality, or other ethylenically unsaturated, free radically reactive functional groups are generally not used.

Generally, liquid plasticizing agents are readily compoundable with one or more elastomeric polymers using an extruder. In addition, liquid plasticizing agents may be delivered directly to a tacky elastomer, if used in the composition, in order to make it less tacky or non-tacky.

Although somewhat more challenging to use, semi-solid (such as petrolatum) and solid plasticizing agents (such as paraffin wax, beeswax, microcrystalline wax, cetyl esters wax) can advantageously be used in compositions where controlled plasticization is desired. For example, hot melt processible compositions can be easily transported and handled prior to melt compounding if the components of the hydrophobic organic matrix, namely the elastomeric polymers and the plasticizing agent, are solid and non-tacky. Once heated to the melting or glass transition temperature of the solid plasticizing agent, the polymer of the matrix is plasticized.

The plasticizing agent is typically used in amounts of from about 1 to 2,000 parts by weight per 100 parts of the hydrophobic polymer.

The hydrophobic organic matrix can include a wide variety of other optional additives in addition to the elastomeric polymer or polymers and the plasticizing agent.

Examples include, but are not limited to, bioactive agents, swelling agents, fillers, pigments, dyes, tackifying agents, crosslinking agents, stabilizers, antioxidants, compatibilizers, extruding aids, chain transfer agents, and combinations thereof.

In certain embodiments, hydrophobic organic matrices can include fillers, which can be inorganic or organic. Examples of inorganic fillers include, but are not limited to, barites, chalk, gypsum, kieserite, sodium carbonate, titanium dioxide, cerium oxide, silica dioxide, kaolin, carbon black, and hollow glass microbeads. Examples of organic fillers include, but are not limited to, powders based on polystyrene, polyvinyl chloride, urea-formaldehyde, and polyethylene. The fillers may be in the form of fibers, such as chopped fibers. Examples of suitable chopped fibers include glass fibers (typically 0.1 millimeter to 1 millimeter long) or fibers of organic origin such as, for example, polyester or polyamide fibers.

In order to confer color to the hydrophobic organic matrix it is possible to use dyes or colored pigments of an organic or inorganic basis such as, for example, iron oxide or chromium oxide pigments or phthalocyanine- or monoazo-based pigments.

The hydrophobic organic matrix can optionally include a bioactive agent. Typically, the bioactive agents are antimicrobial (e.g., antibacterial or antifungal) agents. Such actives are capable of destroying microbes, preventing the development of microbes or preventing the pathogenic action of microbes. An effective amount of a bioactive agent may be added to the present compositions. If use, this amount is typically at least 0.001%, based on the total weight of the composition.

Examples include, but are not limited to, beta-lactam drugs, quinolone drugs, ciprofloxacin, norfloxacin, tetracycline, erythromycin, amikacin, 2,4,4'-trichloro-2'-hydroxy diphenyl ether, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, polyhexamethylene biguanide and its derivatives, streptomycin sulfate, tobramycin sulfate, miconazole hydrochloride, miconazole, ketaconazole, amanfadine hydrochloride, amanfadine sulfate, octopirox, parachlorometa xylenol, nystatin, tolnaftate, pyrithiones (especially zinc pyrithione which is also known as ZPT), dimethyldimethylol hydantoin, methylchloroisothiazolinone/methylisothiazolinone, sodium sulfite, sodium bisulfite, imidazolidinyl urea, diazolidinyl urea, benzyl alcohol, 2-bromo-2-nitropropane-1,3-diol, formalin (formaldehyde), iodopropenyl butylcarbamate, chloroacetamide, methanamine, methyldibromonitrile glutaronitrile (1,2-dibromo-2,4-dicyanobutane), glutaraldehyde, 5-bromo-5-nitro-1,3-dioxane, phenethyl alcohol, o-phenylphenol/sodium o-phenylphenol, sodium hydroxymethylglycinate, polymethoxy bicyclic oxazolidine, dimethoxane, thimersal dichlorobenzyl alcohol, captan, chlorphenenesin, dichlorophene, chlorobutanol, glyceryl laurate, halogenated diphenyl ethers like 2,4,4'-trichloro-2'-hydroxy-diphenyl ether, 2,2'-dihydroxy-5,5'-dibromo-diphenyl ether, phenolic compounds like phenol, 2-methyl phenol, 3-methyl phenol, 4-methyl phenol, 4-ethyl phenol, 2,4-dimethyl phenol, 2,5-dimethyl phenol, 3,4-dimethyl phenol, 2,6-dimethyl phenol, 4-n-propyl phenol, 4-n-butyl phenol, 4-n-amyl phenol, 4-tert-amyl phenol, 4-n-hexyl phenol, 4-n-heptyl phenol, mono- and poly-alkyl and aromatic halophenols such as p-chlorophenol, methyl p-chlorophenol, ethyl p-chlorophenol, n-propyl p-chlorophenol, n-butyl p-chlorophenol, n-amyl p-chlorophenol, sec-amyl pchlorophenol, n-hexyl p-chlorophenol, cyclohexyl p-chlorophenol, n-heptyl p-chlorophenol, n-octyl p-chlorophenol, o-chlorophenol, methyl o-chlorophenol, ethyl o-chlorophenol, n-propyl ochlorophenol, n-butyl o-chlorophenol, n-amyl o-chlorophenol, tert-amyl o-chlorophenol, n-hexyl o-chlorophenol, n-heptyl o-chlorophenol, o-benzyl p-chlorophenol, o-benzyl-m-methyl p-chlorophenol, o-benzyl-m, m-dimethyl p-chlorophenol, o-phenylethyl p-chlorophenol, o-phenylethyl-m-methyl p-chlorophenol, 3-methyl p-chlorophenol, 3,5-dimethyl p-chlorophenol, 6-ethyl-3-methyl p-chlorophenol, 6-n-propyl-3-methyl p-chlorophenol, 6-iso-propyl-3-methyl p-chlorophenol, 2-ethyl-3,5-dimethyl p-chlorophenol, 6-sec-butyl-3-methyl p-chlorophenol, 2-iso-propyl-3,5-dimethyl pchlorophenol, 6-diethylmethyl-3-methyl p-chlorophenol, 6-iso-propyl-2-ethyl-3-methyl p-chlorophenol, 2-sec-amyl-3,5-dimethyl p-chlorophenol 2-diethylmethyl-3,5-dimethyl p-chlorophenol, 6-sec-octyl-3-methyl p-chlorophenol, p-chloro-m-cresol, p-bromophenol, methyl pbromophenol, ethyl p-bromophenol, n-propyl p-bromophenol, n-butyl p-bromophenol, n-amyl p-bromophenol, sec-amyl p-bromophenol, n-hexyl p-bromophenol, cyclohexyl p-bromophenol, o-bromophenol, tert-amyl o-bromophenol, n-hexyl o-bromophenol, n-propyl-m,m-dimethyl o-bromophenol, 2-phenyl phenol, 4-chloro-2-methyl phenol, 4-chloro-3-methyl phenol, 4-chloro-3,5-dimethyl phenol, 2,4-dichloro-3,5-dimethylphenol, 3,4,5,6-terabromo-2-methylphenol, 5-methyl-2-pentylphenol, 4-isopropyl-3-methylphenol, para-chloro-meta-xylenol (PCMX), chlorothymol, 5-chloro-2-hydroxydiphenylmethane, resorcinol and its derivatives including methyl resorcinol, ethyl resorcinol, n-propyl resorcinol, n-butyl resorcinol, n-amyl resorcinol, n-hexyl resorcinol, n-heptyl resorcinol, n-octyl resorcinol, n-nonyl resorcinol, phenyl resorcinol, benzyl resorcinol, phenylethyl resorcinol, phenylpropyl resorcinol, p-chlorobenzyl resorcinol, 5-chloro 2,4-dihydroxydiphenyl methane, 4'-chloro 2,4-dihydroxydiphenyl methane, 5-bromo 2,4-dihydroxydiphenyl methane, and 4'-bromo 2,4-dihydroxydiphenyl methane, bisphenolic compounds like 2,2'-methylene bis(4-chlorophenol), 2,2'-methylene bis(3,4,6-trichlorophenol), 2,2'-methylene bis(4-chloro-6-bromophenol), bis(2-hydroxy-3,5-dichlorophenyl) sulphide, and bis(2-hydroxy-5-chlorobenzyl)sulphide, benzoic esters (parabens) like methylparaben, propylparaben, butylparaben, ethylparaben, isopropylparaben, isobutylparaben, benzylparaben, sodium methylparaben, and sodium propylparaben, halogenated carbanilides (e.g., 3,4,4'-trichlorocarbanilides), 3-trifluoromethyl-4,4'-dichlorocarbanilide, 3,3',4-trichlorocarbanilide, etc.), cationic actives such as benzalkonium chloride, and clotrimazole.

Another class of antimicrobial agents (i.e., actives) which may be useful are the so-called "natural" antibacterial actives, referred to as natural essential oils. These actives derive their names from their natural occurrence in plants. Typical natural essential oil antibacterial actives include oils of anise, lemon, orange, rosemary, wintergreen, thyme, lavender, cloves, hops, tea tree, citronella, wheat, barley, lemongrass, grapefruit seed, cedar leaf, cedarwood, cinnamon, fleagrass, geranium, sandalwood, violet, cranberry, eucalyptus, vervain, peppermint, gum benzoin, basil, fennel, fir, balsam, menthol, *ocmea origanum, Hydastis carradensis, Berberidaceae daceae, Ratanhiae* and *Curcuma longa*. Also included in this class of natural essential oils are the key chemical components of the plant oils, which have been found to provide the antimicrobial benefit. These chemicals include, but are not limited to, anethol, catechole, camphene, thymol, eugenol, eucalyptol, ferulic acid, farnesol, hinokitiol, tropolone, limonene, menthol, methyl salicylate, carvacol, terpineol, verbenone, berberine, ratanhiae extract, caryophellene oxide, citronellic acid, curcumin, nerolidol and geraniol.

The bioactive agent, if used, can be present in the polymer composition in an amount to produce a desired effect (e.g., antimicrobial effect).

The hydrophobic organic matrix can optionally include one or more tackifying agents. The tackifying agent is a resin that is compatible with and modifies the properties of, the elastomeric polymer or polymers. In some embodiments, the elastomeric polymer is a styrenic block copolymer elastomer of the A-B or A-B-A type, where A represents a thermoplastic polystyrene block and B represents a rubbery block of polyisoprene, polybutadiene, or poly(ethylene/butylene). The polystyrene blocks tend to form domains in the shape of spheroids, cylinders, or plates that causes the block copolymer elastomers to have two phase structures. Tackifying agent resins that associate with the rubber phase generally develop tack in the elastomer. Examples of rubber phase associating resins include aliphatic olefin-derived resins, such as the ESCOREZ 1300 series and the WINGTACK series, available from Goodyear; rosin esters, such as the FORAL series and the STAYBELITE Ester 10, both available from Hercules, Inc.; hydrogenated hydrocarbons, such as the ESCOREZ 5000 series, available from Exxon-Mobil; polyterpenes, such as the PICCOLYTE A series; and terpene phenolic resins derived from petroleum or turpentine sources, such as PICCOFYN A100, available from Hercules, Inc. Resins that associate with the thermoplastic phase tend to stiffen the elastomer. Thermoplastic phase associating resins include polyaromatics, such as the PICCO 6000 series of aromatic hydrocarbon resins, available from Hercules, Inc.; coumarone-indene resins, such as the CUMAR series, available from Neville; and other high-solubility parameter resins derived from coal tar or petroleum and having softening points above about 85° C., such as the AMOCO 18 series of alphamethyl styrene resins, available from Amoco, PICCOVAR 130 alkyl aromatic polyindene resin, available from Hercules, Inc., and the PICCOTEX series of alphamethyl styrene/vinyl toluene resins, available from Hercules.

The hydrophilic microparticles can include anionic, cationic, amphoteric, non-ionic polymers, or combinations thereof. Generally, the microparticles are anionic polymers, on-ionic polymers or combinations thereof. Typically, the type and amount of microparticles are selected to provide the desired absorbency to the hydrogel layer.

Generally, the microparticles, when in a substantially nonhydrated form, have an average particle size of 10 micrometers or less, and more typically, 1 micrometer or less. Even more typically, the microparticles have an average particle size of 0.5 micrometer or more when in a substantially nonhydrated form.

Generally, the hydrophilic polymer of the hydrophilic microparticles has a weight average molecular weight of at least 1000.

The hydrophilic microparticles may be present in the polymer layer at any suitable amount. Generally, the hydrophilic microparticles are present in the polymer layer at amounts that range from about 1 to about 60 weight %, or about 4 to about 45 weight % or even about 8 to about 35 weight %.

Typically, the polymer is also dermatologically acceptable and non-reactive with the skin of the patient or with other components of the composition including any antimicrobial agents that may be present therein.

Useful hydrophilic microparticles may be made from a wide variety of synthetically prepared polymers, naturally occurring polymers, or chemically modified naturally occurring hydrophilic polymers. Varieties of polymers that can be used include synthetic polymers prepared from single or multiple monomers. The microparticles can be in an emulsion, such as an inverse emulsion that includes absorbent hydrophilic microparticles. In certain embodiments, the microparticles can be in a dispersion.

Non-limiting examples of such polymers include: polyhydroxyalkyl acrylates and methacrylates (e.g., those prepared from 2-hydroxyethyl acrylate, 2-hydroxyethyl methacrylate, 2-hydroxypropyl acrylate, 2-hydroxypropyl methacrylate, 2,3-dihydroxypropyl methacrylate); poly (meth)acrylic acid and salts thereof (wherein (meth)acrylic acid refers to methacrylic acid and acrylic acid); polyvinyl lactams (e.g., those prepared from N-vinyl lactams such as N-vinyl-2-pyrrolidone, 5-methyl-N-vinyl-2-pyrrolidone, 5-ethyl-N-vinyl-2-pyrrolidone, 3,3-dimethyl-N-vinyl-2-pyrrolidone, 3-methyl-N-vinyl-2-pyrrolidone, 3-ethyl-N-vinyl-2-pyrrolidone, 4-methyl-N-vinyl-2-pyrrolidone, 4-ethyl-N-vinyl-2-pyrrolidone, N-vinyl-2-valerolactam, and N-vinyl-2-caprolactam); polyvinyl alcohols; polyoxyalkylenes; polyacrylamides; polystyrene sulfonates, natural or synthetically modified polysaccarides (e.g., starch, glycogen, hemicelluloses, pentosans, gelatin, celluloses, pectin, chitosan, and chitin), alginates, gums (e.g., Locust Bean, Guar, Agar, Carrageenan, Xanthan, Karaya, alginates, tragacanth, Ghatti, and Furcelleran gums), cellulosics (e.g., those prepared from methyl cellulose, hydroxypropyl methyl cellulose, carboxymethylcellulose, and hydroxypropyl cellulose); polymers prepared from water soluble amides (e.g., N-(hydroxymethyl)acrylamide and N-methacrylamide, N-(3-hydroxpropyl)acrylamide, N-(2-hydroxyethyl)methacrylamide, N-(1,1-dimethyl-3-oxabutyl)acrylamide N-2-(dimethylamine)ethylacrylamide and -methacrylamide, N-3-(dimethylamino)-2-hydroxylpropyllmethacrylamide, and N-1,1-dimethyl-2-(hydroxymethyl)-3-oxabutyllacrylamide)); polymers prepared from water-soluble hydrazine derivatives (e.g., trialkylamine methacrylimide, and dimethyl-(2-hydroxypropyl)amine methacrylimide); monoolefinic sulfonic acids and their salts, (such as sodium ethylene sulfonate, sodium styrene sulfonate and 2-acrylamideo-2-methylpropanesulfonic acid)). Other polymer include those prepared from the following monomers containing nitrogen in the non-cyclic or cyclic backbone of the monomer: 1-vinyl-imidazole, 1-vinyl-indole, 2-vinyl imidazole, 4(5)-vinyl-imidazole, 2-vinyl-1-methyl-imidazole, 5-vinyl-pyrazoline, 3-methyl-5-isopropenyl-pyrazole, 5-methylene-hydantoin, 3-vinyl-2-oxazolidone, 3-methacrylyl-2-oxazolidone, 3-methacrylyl-5-methyl-2-oxazolidone, 3-vinyl-5-methyl-2-oxazolidone, 2- and 4-vinyl-pyridine, 5-vinyl-2-methyl-pyridine, 2-vinyl-pyridine-1-oxide, 3-isopropenyl-pyridine, 2- and 4-vinyl-piperidine, 2- and 4-vinyl-quinoline, 2,4-dimethyl-6-vinyl-s-triazine, and 4-acrylyl-morpholine.

In some embodiments, the microparticles are prepared from amine-containing organic polymers. Generally, the amine-containing hydrophilic polymer includes a quaternary amine, and more typically, the amine-containing polymer is a quaternary ammonium salt of an organic polymer. Examples include, but are not limited to, polymerization products of cationic vinyl monomers as disclosed in EP 0 489 967 A1, and inherently antimicrobial quaternary amine polymers as described in U.S. Pat. No. 6,039,940.

In some particularly desirable embodiments, the microparticles are prepared from carboxylic acid-containing organic polymers. Examples of such microparticles include sodium polyacrylate (i.e., a copolymer of sodium acrylate and acrylic acid) microparticles such as those commercially available under the trade designation SALCARE SC91 from Ciba Specialty Chemicals (High Point, N.C.).

Examples of suitable microparticles are described in European Patent Documents EP 172,724 and EP 126,528, which describe microparticles made by reverse phase polymerization that have a dry particle size below 4 micrometers.

Other suitable polymeric microparticles can be prepared from a quaternary ammonium monomer, which is a salt having an organo-ammonium group and a monoethylenically unsaturated group. For certain embodiments, the quaternary ammonium monomer has the following general Formula (I):

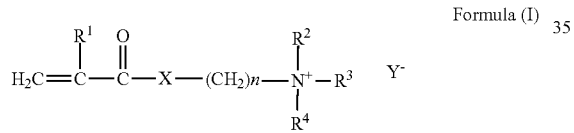

Formula (I)

wherein: n is 2 to 10, typically 2 to 3; $R^1$ is H or $CH_3$; $R^2$, $R^3$, and $R^4$ are each independently linear or branched organic groups, generally having 1 to 16 carbon atoms (on average); X is O or NH; and $Y^-$ is an acceptable anionic counterion to the $N^+$ of the quaternary ammonium group (e.g., one that does not adversely affect the polymerization of the monomers or antimicrobial activity of an added antimicrobial agent).

Generally, $R^2$, $R^3$, and $R^4$ are each independently alkyl, aryl, alkaryl, or aralkyl groups. Alkyl groups are generally lower alkyl, having 1 to 16 carbon atoms (on average) with methyl and ethyl groups being particularly suitable. Aryl is generally phenyl but can be any suitable aromatic moiety such as those selected from the group consisting of phenyl, thiophenyl, naphthyl, biphenyl, pyridyl, pyrimidinyl, pyrazyl, pyridazinyl, furyl, thienyl, pyrryl, quinolinyl, bipyridyl, and the like. Representative of an aralkyl grouping is benzyl and representative of an alkaryl grouping is tolyl. X is generally O. Representative counterions ($Y^-$) are $Cl^-$, $Br^-$, $HSO_4^-$, $CH_3CH_2OSO_3^-$, and $CH_3OSO_3^-$, with the chloride salts being particularly suitable. Alkyl groups can be straight or branched chain and alkyl and aryl groups can be substituted by non-interfering substituent that do not obstruct with the functionality of the polymers.

Useful copolymerizable quaternary ammonium monomers include, but are not limited to, those selected from 2-(meth)acryloxyethyl trialkyl ammonium halides and sulfates, and mixtures thereof. Examples of such compounds include, but are not limited to, 2-(meth)acryloxyethyl trimethyl ammonium chloride, $CH_2$=$CR^1CO_2CH_2CH_2N(CH_3)_3Cl$; 2-(meth)acryloxyethyl trimethyl ammonium methyl sulfate, $CH_2$=$CR^1CO_2CH_2CH_2N(CH_3)_3OSO_2OCH_3$; 2-(meth)acryloxyethyl methyl diethyl ammonium methyl sulfate, $CH_2$=$CR^1CO_2CH_2CH_2N(CH_3)(C_2H_5)_2OSO_2OCH_3$; 2-(meth)acryloxyethyl dimethyl benzyl ammonium chloride, $CH_2$=$CR^1CO_2CH_2CH_2N(CH_3)_2(C_6H_5CH_2)Cl$ (where $R^1$ is a hydrogen atom or a methyl group, all of the preceding monomers available from Ciba Specialty Chemicals, Woodbridge, N.J.); 2-(methylacryloxy)ethyl dimethyl hexadecyl ammonium bromide, $CH_2$=$C(CH_3)CO_2CH_2CH_2N(CH_3)_2(C_{16}H_{33})Br$ (described in U.S. Pat. No. 5,437,932 (Ali et al.)); and the like. Various combinations of these monomers can be used if desired. Due to their availability, effectiveness in reinforcing (meth)acrylate polymers and their antimicrobial activity, particularly suitable quaternary ammonium monomers are 2-acryloxyethyl trimethyl ammonium methyl sulfate and 2-acryloxyethyl methyl diethyl ammonium methyl sulfate. Such monomers are typically hydrophilic. Various combinations of other monoethylenically unsaturated monomers that are reinforcing monomers can be used in the polymers of the present disclosure. Such reinforcing monomers include, but are not limited to, acrylic acid, methacrylic acid, ethylene vinyl acetate, and N,N-dimethylacrylamide.

As an alternative approach to providing polymers that contain a quaternary ammonium functional unit, it is possible to start with an amine monomer and form the quaternary ammonium unit following polymerization. For certain embodiments, the amine monomers have the following general Formula (II):

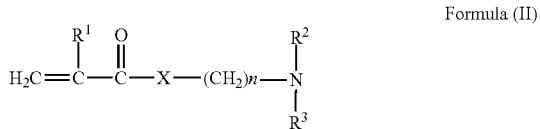

Formula (II)

wherein n, $R^1$, $R^2$, $R^3$, and X are the same as defined for Formula (I).

As stated above, the microparticles can be in an emulsion, such as an inverse emulsion. One type of inverse emulsion can be defined as a continuous hydrophobic liquid phase (e.g., mineral oil) and hydrophilic polymer particles dispersed within the hydrophobic liquid phase. Suitable examples of such materials are described in European Patent Document EP 126,528. Such a material is commercially available under the trade designation SALCARE from Ciba Specialty Chemicals (High Point, N.C.). Suitable examples include SALCARE 95 and 96 which include a cationic homopolymer of the methyl chloride quaternary salt of 2-(dimethylamino)ethyl methacrylate (CAS No. 26161-33-1).

Other amine-containing polymers can be made from amine-containing monomers as described below and in European Patent Document EP 489,967 and U.S. Pat. No. 6,039,940.

Monomers can be polymerized using techniques such as solution polymerization, emulsion polymerization, bulk polymerization, suspension polymerization, and the like. Each polymerization method can have drawbacks and benefits. In particular, emulsion polymerization and suspension polymerization are desirable because the molecular weight of the polymer becomes high; solution polymerization is desirable because the molecular weight distribution is comparatively narrow; and bulk polymerization is desirable because no solvent is used.

In such polymerizations, initiators can be used to generate free-radicals upon the application of activating energy such as those conventionally used in the polymerization of ethylenically unsaturated monomers. Included among useful free-radical initiators are the thermally activated initiators such as organic peroxides, organic hydroperoxides, and azo-compounds. Representative examples of such initiators include, but are not limited to, benzoyl peroxide, tertiary-butyl perbenzoate, diisopropyl peroxydicarbonate, cumene hydroperoxide, azobis(isobutyronitrile), and the like. Generally, the thermal initiators are typically used in amounts from 0.01 to 5 percent by weight of monomer.

The polymerization of the polymer may also be initiated by photoinitiators. Such photochemically activated initiators are well known and have been described in the polymerization art; e.g., Chapter II of "Photochemistry" by Calvert and Pitts, John Wiley and Sons (1966) and in Progress in Organic Coatings, 13, 123-150 (1985). Representative examples of such initiators include benzoin, benzoin methyl ether, benzoin isopropyl ether, benzoin isobutyl ether, and 2-hydroxy-2-methyl-1-phenyl-1-propane, benzildimethylketal and benzildiethylketal, 2-hydroxy-1-(4-(2-hydroxyethoxy)phenyl)-2-methyl-1-propanone. A suitable photoinitiator is 2-hydroxy-1-(4-(2-hydroxyethoxy)phenyl)-2-methyl-1-propanone. Generally, photoinitiators are used in amounts from 0.01 to 5 percent by weight of monomer.

The polymerization of the polymer may also be initiated by electromagnetic radiation such as electron beams and the gamma-rays of cobalt 60, and the like. The irradiation dose is typically between 1 and 100 kGy.

The polymer may be crosslinked by adding a crosslinking compound or through electron beam or gamma radiation. A crosslinking compound can be a multi-ethylenically unsaturated compound wherein the ethylenic groups are vinyl groups, allyl groups, and/or methallyl groups bonded to nitrogen or oxygen atoms. Exemplary compounds include divinyl, diallyl or dimethallyl esters (e.g., divinyl succinate, divinyl adipate, divinyl maleate, divinyl oxalate, divinyl malonate, divinyl glutarate, diallyl itaconate, diallyl maleate, diallyl fumarate, diallyl diglycolate, diallyl oxalate, diallyl adipate, diallyl succinate, diallyl azelate, diallyl malonate, diallyl glutarate, dimethallyl maleate, dimethallyl oxalate, dimethallyl malonate, dimethallyl succinate, dimethallyl glutarate, and dimethallyl adipate), divinyl, diallyl or dimethallyl ethers (e.g., diethyleneglycol divinyl ether, butanediol divinyl ether, ethylene glycol divinyl ether, ethylene glycol diallyl ether, diethylene glycol diallyl ether, butane diol diallyl ether, ethylene glycol dimethallyl ether, diethylene glycol dimethallyl ether, and butane diol dimethallyl ether), divinyl, diallyl or dimethallyl amides including bis(N-vinyl lactams), (e.g., 3,3'-ethylidene bis(N-vinyl-2-pyrrolidone)), and divinyl, diallyl or dimethallyl ureas.

In addition to the hydrophilic microparticles, additional hydrophilic particles may be optionally included in the hydrogel layer. These particles, in contrast with the hydrophilic microparticles typically, when in a substantially non-hydrated form, have an average particle size of 10 micrometers or more. These larger particles can aid in the absorptive properties of the hydrogel layer. Typically, if used, these larger hydrophilic particles are present at less than about 20 weight %. More typically, the larger hydrophilic particles are present in amounts of from 0.5 to 15 weight %.

The use of the particles with an average particle size of at least 10 micrometers has been found to be particularly desirable when sterilization by gamma radiation is contemplated. While not wishing to be bound by theory, it is believed that at certain concentrations of water, these larger particles can act as stabilizers during gamma irradiation such that degradation reactions of the microparticles are reduced. The reduction of degradation reactions leads to a greater retention of the absorptive properties of the hydrogel layer.

The optional larger particles can be prepared from the same or similar polymer compositions as the hydrophilic microparticles described above, or may have a different composition. Examples of suitable larger particles include carboxymethyl cellulose powders such as AC-DI-SOL Sodium Croscarmellose, a crosslinked polymer of carboxymethyl cellulose sodium, commercially available from FMC Biopolymer Philadelphia, Pa.

The hydrogel layer may further comprise an optional porous web. The porous web can act as a supporting layer or a carrier layer for the hydrogel layer or the porous web may act as a backing layer for the entire wound dressing article. Porous webs are desirable because they readily allow the passage of wound fluids, moisture vapor, and air. Hence, the porous webs are typically liquid permeable. A wide variety of materials may be used to prepare the porous web. Suitable materials are generally flexible, and may be fabric, non-woven or woven polymeric films, metallic, paper, and/or combinations thereof. For certain embodiments it may be desirable to use an open- or closed-cell foam, such as those disclosed in U.S. Pat. Nos. 6,548,727 and 5,409,472.

Suitable porous webs include knits, wovens (e.g., cheese cloth and gauze), nonwovens (including spun-bonded nonwovens), extruded porous sheets, and perforated sheets. The apertures (i.e., openings) in the porous webs are of sufficient size and sufficient number to facilitate high breathability. In some embodiments, the porous webs have at least 1 aperture per square centimeter. In some embodiments, the porous substrates have no greater than 225 apertures per square centimeter. In some embodiments, the apertures have an average opening size (i.e., the largest dimension of the opening) of at least 0.1 millimeter. In some embodiments, the apertures have an average opening size (i.e., the largest dimension of the opening) of no greater than 0.5 centimeter. In some embodiments, the porous webs have a basis weight of at least 5 grams/meter$^2$. In some embodiments, the porous webs have a basis weight of no greater than 200 grams/meter$^2$.

The porous webs are generally flexible yet resistant to tearing. The thickness of the porous web is typically at least 0.0125 millimeter. In some embodiments, the thickness of the porous web is no greater than 4 millimeters.

The porous webs may be opaque or translucent or can come in a variety of different colors. Materials of the porous web may include a wide variety of materials including paper, natural or synthetic fibers, threads and yarns made from materials such as cotton, rayon, wool, hemp, jute, nylon, polyesters, polyacetates, polyacrylics, alginates, ethylene-propylene-diene rubbers, natural rubber, polyesters, polyisobutylenes, polyolefins (e.g., polypropylene polyethylene, ethylene propylene copolymers, and ethylene butylene copolymers), polyurethanes (including polyurethane foams), vinyls including polyvinylchloride and ethylene-vinyl acetate, polyamides, polystyrenes, fiberglass, ceramic fibers, and/or combinations thereof.

In some embodiments, the porous web may be coated on one or both major surfaces. These coatings may be, for example primer coatings or release agent coatings to modify the surface properties of the porous web.

The hydrogel layer or the entire wound dressing article may be covered by one or more protective liners. The protective liner protects the exposed surface of the hydrogel layer or the entire article from contamination prior to use and can function to facilitate extraction of the article from a package and in handling the article. In some embodiments, the protective liner is a film, such as a polyester film, with no surface treatments such as non-stick treatments. In other embodiments, the protective liner comprises a release liner. The term "release liners" as used herein refers to articles containing at least one release surface. Exemplary release liners include those prepared from paper (e.g., Kraft paper) or polymeric material (e.g., polyolefins such as polyethylene or polypropylene, ethylene vinyl acetate, polyurethanes, polyesters such as polyethylene terephthalate, and the like). At least some release liners are coated with a layer of a release agent such as a silicone-containing material or a fluorocarbon-containing material. Exemplary release liners include, but are not limited to, liners commercially available from CP Film (Martinsville, Va.) under the trade designation "T-30" and "T-10" that have a silicone release coating on polyethylene terephthalate film and those available from Loparex, Inc., Willowbrook, Ill.

As mentioned above, the protective liner may cover the hydrogel layer or may cover the entire wound dressing article. In some embodiments, portions of the wound dressing article contain one or more adhesive layers to adhere the wound dressing to a user. These adhesive layers may be covered with a release liner, and the release liner may be the same or different from the protective liner covering the hydrogel layer.

The sterilized wound dressings of this disclosure are prepared by providing a polymer layer, applying an aqueous solution to the polymer layer to form a hydrogel layer, optionally placing the wound dressing article in non-porous package, and applying electron beam radiation to the article.

The polymer layer is prepared by forming a polymer layer composition. The polymer layer composition comprises at least one elastomeric polymer, an optional plasticizer, hydrophilic microparticles and any optional components such as those described above. A variety of different methods, including hot-melt processes and solvent-based processes can be used to prepare and coat the polymer layer compositions. In some embodiments, the polymer layer compositions are prepared by hot mixing without a solvent (so-called hot-melt process), by blending an elastomer, an optional plasticizer, and other optional additives, and then adding substantially nonhydrated hydrophilic microparticles either as a finely divided powder or as an inverse emulsion and extruding, molding or hot-melt coating the hot-melt polymer layer composition to form the wound dressing article. In other embodiments, the polymer layer components are mixed in solvent and solvent cast to form the wound dressing article.

The polymer layer compositions may be coated onto a substrate. The substrate may be an optional porous web that becomes part of the polymer layer, or the substrate may be a backing or other suitable substrate that is part of the overall wound dressing article, or the substrate may be a carrier substrate such as a release liner that does not become a permanent part of the wound dressing article.

The choice of processing method depends upon a variety of factors including whether the elastomeric polymers are melt processable. The elastomeric polymers are melt processable if they are fluid or pumpable, and they do not significantly degrade or gel at the temperatures used to melt process (e.g., extruding or compounding) the polymer layer composition (e.g., at least 50° C. and up to 300° C.).

Continuous melt process forming methods include drawing the extruded polymer layer composition out of a film die and subsequently contacting a moving substrate. As described above, the substrate may be an optional porous web that becomes part of the polymer layer, or the substrate may be a backing or other suitable substrate that is part of the overall wound dressing article, or the substrate may be a carrier substrate such as a release liner that does not become a permanent part of the wound dressing article. Another continuous forming method involves directly contacting the extruded polymer layer composition to a moving substrate. In this method, the extruded polymer layer composition can be applied to a moving substrate using a die having flexible die lips such a reverse orifice coating die and other contact dies using rotating rods. The polymer layer composition can also be extruded in the form of continuous fibers and blown micro-fiber webs as disclosed in Wente, Van A., "Superfine Thermoplastic Fibers," Industrial Engineering Chemistry, Vol. 48, pp. 1342-1346; Wente, Van A. et al., "Manufacture of Superfine Organic Fibers," Report No. 4364 of the Naval Research Laboratories, published May 25, 1954; and U.S. Pat. Nos. 5,176,952 and 3,841,953. After melt process forming, the polymer layer composition is solidified by quenching using either direct methods, such as chill rolls or water baths, or indirect methods, such as air or gas impingement, or both.

In some embodiments, the molten polymer layer composition may be coated on a porous web. When a porous web is coated, the process of coating the porous substrate with the composition typically allows the yarns, filaments, or film to be properly trapped in the composition, while leaving most of the apertures unobstructed by the composition. Depending on the structure of the support used, the amount of composition employed will vary over a wide range (typically from 25 grams per square meter ($g/m^2$) to 500 $g/m^2$, and more typically from 40 $g/m^2$ to 200 $g/m^2$). The molten polymer layer composition may be coated on a porous web using a continuous process in which the porous web is directed over a first coating roll covered with a layer of molten polymer layer composition having a predetermined thickness, and then over a second roll which removes the polymer layer composition lying within the apertures of the porous web. The substrate thus covered with polymer layer composition only on the yarns, filaments, or film is then cooled in a stream of air so that the composition cannot flow and remains uniformly distributed around the yarns, filaments, or film. If necessary, a system producing a laminar stream of air is provided, which system is able both to correct the distribution of the composition around the yarns, filaments, or film and to unblock any substrate apertures, which would not have been open in the previous step of the process.

According to a variant of this process, a porous web can be passed through a bath of molten polymer layer composition (for example, at a temperature of 120° C. to 200° C.). The porous web covered with molten polymer layer composition is then passed between two fixed rolls pressed against each other with a predetermined gap, so as to remove the excess polymer layer composition. The amount of polymer layer composition remaining on the yarns, filaments, or film depends upon on the gap set between the fixed rolls. The coated porous web is then cooled and treated in a manner similar to the previous process.

Solvent casting may also be used to prepare the wound dressing articles. This method typically employs a common solvent, selected for compatibility with the polymer layer composition components. Such common solvents include, for example, toluene, tetrahydrofuran, ethyl acetate, and the like. Specific selection of a common solvent will depend upon a variety of criteria and is within the knowledge of one of skill in the art. In the solvent casting method, the materials included in the polymer layer composition are blended to form a uniform mixture, then coated onto a substrate using a known coating technique such as curtain coating, die coating, knife coating, roll coating, spray coating, and printing techniques such as screen printing, gravure printing, and inkjet printing. A particularly desirable coating method is knife coating. As described above, the substrate may be an optional porous web that becomes part of the polymer layer, or the substrate may be a backing or other suitable substrate that is part of the overall wound dressing article, or the substrate may be a carrier substrate such as a release liner that does not become a permanent part of the wound dressing article. The solvent is then removed from the coated substrate, usually with the aid of a drying oven for a time and temperature selected to remove any undesirable level of residual solvent.

The polymer layer, however prepared, may be subjected to additional processing steps prior to the application of an aqueous solution. For example, the coated polymer layers may cut into a desirable size and shape, additional layers such as a backing layer may be added, and the like.

The polymer layer, whatever method or combination of methods used to prepare it, then has an aqueous solution applied to it. The aqueous solution at least partially swells the hydrophilic microparticles of the hydrogel layer. The aqueous solution may be water, such as sterilized or deionized water, or it may contain dissolved or water-miscible components such as salts, sugars and the like. Additionally, the aqueous solution may also contain a preservative such as parabens, benzoic acid, silver compounds, polyhexamethylene biguanide and its derivatives, or the like.

While not wishing to be bound by theory, it is believed that dispersion of the hydrophilic microparticles within the hydrophobic organic matrix and applying an aqueous solution to the polymer layer prior to irradiation by electron beam radiation helps to protect the hydrophilic microparticles from degradation reactions that can occur due to free radical formation reactions that can occur upon exposure to electron beam radiation. For example, electron beam radiation can cause crosslinking or degradation of the absorptive polymeric components within the hydrogel layer and this crosslinking or degradation can cause a decrease in the absorptive properties of the hydrogel layer. However, dispersing the hydrophilic microparticles in a hydrophobic organic matrix and applying an aqueous solution to the polymer layer prior to exposure to electron beam radiation helps to diminish changes in the properties, especially absorptive properties, of the hydrogel layer. As mentioned previously, especially in instances where gamma radiation is used, the presence of hydrophilic particles with an average particle size of greater than 10 micrometers, in conjunction with certain levels of aqueous solution and the hydrophilic microparticles, can help to minimize the degradation reactions and consequent loss of absorptive properties of the hydrogel layer.

The application of the aqueous solution may be carried out by a variety of techniques including coating techniques. Examples of suitable coating techniques include curtain coating, die coating, knife coating, roll coating, dip coating, spray coating, and printing techniques such as screen printing, gravure printing, and inkjet printing.

A variety of different techniques can be used to describe the amount of aqueous solution that is suitable to be applied to the polymer layer. The amount of aqueous solution added can be described by a weight ratio. The weight ratio is the weight of added aqueous solution to the dry weight of the hydrogel layer. In some embodiments, this ratio is in the range of 0.1:1 to 10:1. In other embodiments, this ratio is 0.5:1 to 5.0:1 or even 1.0:1 to 2.5:1.

Another related method for characterizing the amount of aqueous solution that is suitable to be applied to the polymer layer is the weight ratio of applied aqueous solution to the dry weight of microparticles in the polymer layer. In some embodiments, this ratio is in the range of from 0.2:1 to 30:1. In other embodiments, this ration may be from 0.2:1 to 20:1, 0.2:1 to 10:1 or even 0.2:1 to 5:1.

Another method for characterizing the amount of aqueous solution that is suitable to be applied to the polymer layer is to describe the aqueous solution content of the hydrogel layer after the addition of the aqueous solution to the polymer layer. Typically the hydrogel layer contains at least 10% aqueous solution by weight. In some embodiments, the hydrogel layer contains at least 25% aqueous solution by weight, or even 75% aqueous solution by weight.

If desired, the hydrogel layer can be covered with one or more protective films or liners. As described above, these protective films or liners may be release liners or they may be films that do not contain a nonstick treatment. If desired, the coated substrate can be cut into individual compresses, of sizes suitable for use.

The formed wound dressing may be characterized by its density. The density of the wound dressing depends on the form of the hydrogel layer (whether, for example, the hydrogel layer is essentially continuous or porous) and the from of the support substrate, if present. For example, the density of a non-porous hydrogel layer typically can range from about 0.8 grams per cubic centimeter ($g/cm^3$) to about 1.2 $g/cm^3$. The density of a porous hydrogel layer typically ranges from about 0.10 $g/cm^3$ to about 0.90 $g/cm^3$, or even 0.2 $g/cm^3$ to about 0.7 $g/cm^3$.

In some embodiments, including some particularly desirable embodiments, it is desirable to place the formed wound dressing that has had an aqueous solution applied to it, into a package. Typically the package is a non-porous package. Hydrogel wound dressings are typically packaged in a non-porous sealed package to prevent the loss of significant moisture from the dressing over time.

Examples of wound dressing packages suitable for use with the methods of this disclosure include, for example polymeric packages and foil packages. A wide variety of polymeric materials may be used to make non-porous packages suitable for use with hydrogel wound dressings. The packaging material may be, for example, polyethylene, polypropylene, copolymers of ethylene and propylene, polybutadiene, ethylene-vinyl acetate, ethylene-acrylic acid, or ionomeric films. Suitable foil packages include aluminum foil packages. In some embodiments, the packaging material may be used as sheets of material which are placed above and below the wound dressing and then sealed on four sides to generate the package. In other embodiments, a pre-made pouch is utilized which has 3 sides already sealed. After the wound dressing article is placed within the pouch the fourth side is sealed to form the package. Sealing of the package can be achieved by heat sealing (i.e. by the application of heat and pressure to form a seal) or the use of adhesive sealants can be used to seal the packages (for example pressure sensitive adhesive sealants or cold seal sealants). Typically, heat sealing is used. Additionally, packaging systems can be used which include placing the wound dressing in a porous package that is then placed in a non-porous package, such as a foil package. The foil package prevents moisture loss prior to use and the porous package permits easy handling during use.

Once the aqueous solution has been applied to the polymer layer, the dressing can be sterilized by application of radiation. In many embodiments, this radiation is electron beam radiation, but in certain embodiments the radiation is gamma radiation. This irradiation can be carried out whether or not the wound dressing article is contained within a package.

Electron beam radiation can be a desirable method to sterilize the wound dressings of this disclosure, because gamma radiation can, in some embodiments, cause additional crosslinking or degradation of the water containing microparticles within the hydrogel wound dressing causing the loss of absorptive performance. In addition, gamma radiation may be less desirable because gamma radiation typically requires hours of radiation exposure to achieve sterilization. Exposure of the wound dressings of this disclosure to electron beam irradiation does not produce a significant loss of absorptive performance. However, in some embodiments, gamma radiation is equally suitable.

The exposure times and levels of radiation doses applied to the wound dressings to achieve sterilization can vary based upon a variety of factors, including the electron beam equipment used as well as the inherent bioburden levels present in the dressing. Typically, to achieve sterilization of a wound dressing, a Sterility Assurance Level (SAL) of $10^{-6}$ is required. This SAL level is typically achieved by exposing the wound dressing to a minimum cumulative electron beam irradiation dose. Depending on the bioburden levels in an unsterilized dressing and the size of the dressing, the minimum cumulative dose can range from about 10 kGy to about 35 kGy. Typically the minimum cumulative dose is about 15 to 30 kGy. The required electron beam radiation dose to achieve sterility can be done in a single pass or multiple passes through the electron beam sterilizer. For example, exposing the wound dressing to 5 sterilization cycles using a dose of 5 kGy per cycle would be similar to exposing the wound dressing to one dose of 25 kGy of electron beam radiation. Due to labor and time constraints, it is generally desirable to minimize the number of passes that a wound dressing experiences through the electron beam sterilizer. Typically, it is desirable that the number of passes through the sterilizer be five or less, and it may be even more desirable for the number of passes to be two or less. Exposure time may be viewed as the time a sample to be sterilized is exposed to the electron beam radiation. Typically the exposure time is less than 5 minutes. More typically, the exposure time is less than 1 minute. In some embodiments, the exposure time is less than about 20 seconds.

As discussed previously, gamma irradiation may also be applied to effect sterilization in some embodiments. In particular, embodiments in which the polymer layer contains not only hydrophilic microparticles, but also particles with at least 10 micrometer average particle size are suitable for sterilization by gamma radiation. Once the aqueous solution has been applied at certain levels to a polymer layer containing absorbent particles of at least 10 micrometer average particle size, the dressing can be sterilized by application of gamma radiation. This irradiation can be carried out whether or not the wound dressing article is contained within a package.

Gamma radiation is a suitable method to sterilize the wound dressings of this disclosure, if the wound dressing contains absorbent particles of at least 10 micrometer average particle size and contains a weight ratio of water to microparticles in the polymer layer of from between about 0.2:1 to about 6:1. Under these embodiments, exposure of the wound dressings of this disclosure to gamma irradiation does not produce a comparable loss of absorptive performance.

The levels of gamma radiation doses applied to the wound dressings to achieve sterilization are similar to those described for electron beam radiation discussed above. Typically the exposure time to achieve sterilization for gamma irradiation is measured in hours.

The sterilized wound dressings of this disclosure retain much of their absorptive capacity even after undergoing sterilization by exposure to electron beam radiation. The absorptive capacity of the wound dressings can be measured using the Absorbent Capacity Test Method described in the Examples section below. In this method a sample dressing is weighed prior to (Weight 1 or W1) and after (Weight 2 or W2) soaking in an aqueous solution for 2 hours at 25+/−2° C. The Absorbent Capacity is calculated from the equation:

$$\text{Absorbent Capacity}=(W2-W1)/W1\times 100.$$

Comparison of identical samples, one of which has not been exposed to radiation and one that has been exposed to radiation, permits the determination of the amount of retention of absorbent capacity after irradiation. The sterilized articles of this disclosure typically retain at least 40% of the absorptive capacity of identical dressings that have not been sterilized. More typically, the sterilized articles of this disclosure typically retain at least 60% of the absorptive capacity of identical dressings that have not been sterilized. In some embodiments, the sterilized articles of this disclosure typically retain at least 80% of the absorptive capacity of identical dressings that have not been sterilized.

EXAMPLES

These examples are merely for illustrative purposes only and are not meant to be limiting on the scope of the appended claims. All parts, percentages, ratios, etc. in the examples and the rest of the specification are by weight, unless noted otherwise. Solvents and other reagents used were obtained from Sigma-Aldrich Chemical Company; Milwaukee, Wis. unless otherwise noted.

Table of Abbreviations

| Abbreviation or Trade Designation | Description |
|---|---|
| Mineral Oil | USP grade mineral oil, commercially available as Kaydol Mineral Oil from Crompton Corporation, formerly Witco Corporation. |
| Emulsion-1 | A 50 weight percent solids cosmetic grade emulsion having microparticles of a chemically crosslinked hydrophilic anionic copolymer of acrylic acid and sodium acrylate that are dispersed in mineral oil and contains a non-ionic surfactant, commercially available from Ciba Specialty Chemicals, High Point, NC, (now part of BASF, Florham Park, NJ) as "SALCARE SC91". |
| Emulsion-2 | A 50 weight percent solids cosmetic grade emulsion having microparticles of a chemically crosslinked hydrophilic anionic copolymer of acrylic acid and sodium acrylate that are dispersed in mineral oil and contains a non-ionic surfactant, commercially available from Ciba Specialty Chemicals, High Point, NC, (now part of BASF, Florham Park, NJ) as "SALCARE SC95". |
| Block Copolymer-1 | A white powder, mineral oil extended linear triblock copolymer based on styrene and ethylene/butylene with a polystyrene content of 33%, and a nominal oil content of 45.5% wt (90 parts/100 parts rubber (phr)), coomercially available from Kraton Polymers, Houston, TX as "KRATON G4609H". |
| Antioxidant-1 | Commercially available from Ciba Specialty Chemicals, High Point, NC, (now part of BASF, Florham Park, NJ) as "IRGANOX 1010". |
| Water | USP Sterile water Commercially available from Baxter, Deerfield, IL. |
| PHMB | Polyhexamethylene biquanide, 20% w/w in water, commercially available from Arch Chemicals, Inc., Norwalk, CT, as "COSMOCILCQ". |
| CMC | A crosslinked polymer of carboxymethylcellulose sodium, commercially available as AC-DI-SOL Sodium Croscarmellose from FMC Biopolymer, Philadelphia, PA. |
| Polyester Scrim | Style M1763 polyester knitted scrim, scour white, no finish commercially available from Gehring Textiles, Inc., Garden City, NY. |
| Cellulose Gum | Carboxymethyl cellulose, (CMC-PE32 FG-X) commercially available from S & G Resources, Inc., Medfield, MA. |
| Foil/Foil Package | Peelable polyester foil/foil pouch (185 mm × 140 mm) with three sides sealed, commercially available as TPS-4048/TPC-0769 from Tolas Healthcare Packaging, Feasterville, PA. |
| Release Liner-1 | A polyester liner, 50 micrometers thick, with 4400 release chemistry on one side commercially available from Loparex, Inc., Willowbrook, IL. |
| Sodium chloride, NaCl | Sodium chloride (used in making Ringers solution), commercially available from VWR International, West Chester, PA. |
| Calcium chloride, $CaCl_2$ | Calcium chloride (used in making Ringers solution), commercially available from VWR International, West Chester, PA. |
| Saline Solution | A 0.9% (w/w) sodium chloride solution, sterile, commercially available from Phoenix Scientific, Inc., St. Joseph, MO. |

Test Methods

Absorbent Capacity

The absorbent capacity of a sample was determined by first weighing the sample before starting the absorbent capacity test (i.e., after addition of water and/or irradiation, and after removing from packaging). This weight was recorded as W1. The sample was allowed to soak in an aqueous solution for 2 hours. The test aqueous solution used was either water, a 0.9% (w/w) sodium chloride solution, or Ringer's solution which is an aqueous solution containing 142 mmol/liter sodium chloride and 2.5 mmol/liter calcium chloride. The aqueous solution used for each test is specified for each example. After 2 hours at 25+/−2° C., the sample was removed from the aqueous solution using forceps and allowed to drip excess moisture from the sample for approximately 30 seconds before recording its final weight, recorded as W2. The absorbent capacity (%) was then determined by:

Absorbent Capacity(from initial weight)=$(W2−W1)/W1 \times 100$

A similar method to determine the absorbent capacity of a sample was to weigh the sample dry (i.e., before addition of water to the sample). This weight is $W_{dry}$. After addition of water and further processing, such as packaging, equilibration, and/or irradiation, the sample was allowed to soak in an aqueous solution for 2 hours at 25+/−2° C. After 2 hours, the sample was removed from the aqueous solution using forceps and allowed to drip excess moisture from the sample for approximately 30 seconds before recording its final weight, W2. The absorbent capacity (%) was then determined by:

Absorbent Capacity(from initial dry weight)=$(W2−W_{dry})/W_{dry} \times 100$

For some examples the Absorbent Capacity (%) is reported, for other examples the W2 and W1 or $W_{dry}$ values are reported, because it not possible to directly compare Absorbent Capacities for W1 samples to $W_{dry}$ samples because W1 samples have some Absorbent Capacity already occupied with an added aqueous solution.

Examples 1-4 and Comparative Examples C1-C12

Comparative Example C1

A mixture of approximately 18.7 parts (w/w) Block Copolymer-1, 40.2 parts Mineral Oil containing 1% (w/w) Antioxidant-1, 39.2 parts Emulsion-1, and 1.9 parts CMC powder were fed to, melted, and compounded in a twin screw extruder (Haake 25 mm diameter, fully intermeshing counter-rotating) operated at 300 rpms. The Block Copolymer-1 and the CMC were gravimetrically fed to the feed throat of the extruder at 9.35 g/min and 0.95 g/min, respectively. Zones 1 and 2 of the extruder were set at 204° C. The Mineral Oil with Antioxidant-1 was heated and fed into Zone 3 (set at 176° C.) of the extruder at a rate 20.1 g/min. The Emulsion-1 was metered to Zone 5 (set at 149° C.) at a rate of 19.6 grams/min using a zenith gear pump. The remaining two zones of the extruder and the transport hose were also maintained at 149° C. The melt pump out of the extruder was set at 218° C. The compounded hot gel was then coated onto an 18 cm wide Polyester Scrim using the method described in Examples 1 and 2 of US Patent Publication No. 2005/012350 except the steel rolls and die were controlled to 157° C. The gel coated scrim was wound up with an inserted sheet of Release Liner-1. The coating weight of the gel on the scrim was 1.1 grams/24 in$^2$. The thickness of the gel coated scrim was about 0.5 mm. The gel coated scrim was placed between two sheets of Release Liner-1 with the release side of the liner facing the gel. Samples of 7.5 cm×10 cm pieces of gel coated scrim between liners were cut out, placed in a Foil/Foil package, and the opening of the package was heat sealed using a bar sealer. Five samples of the gel coated scrim were removed from their packages and tested for Absorbent Capacity (from initial weight) using the Test Method described above using Ringer's solution. The results are shown in Table 1.

Comparative Example C2

Samples of the gel coated scrim in Comparative Example C1 were prepared and packaged as described in Comparative Example C1 except that the packaged samples were gamma irradiated in two passes using a Cobalt-60 source at 22.3-23.6 kGy for the first pass. After the second pass through the gamma irradiation source, the total dose was 29.5-31.0 kGy. Five samples of the gel coated scrim were removed from their packages and tested for Absorbent Capacity (from initial weight) using the Test Method described above using Ringer's solution. The results are shown in Table 1.

Comparative Example C3

Samples of 7.5 cm×10 cm gel coated scrim prepared as described in Comparative Example C1 were placed on a sample of Release Liner-1 and coated with 0.7 grams of sterile water containing 500 ppm PHMB. After adding the sterile water solution, a second sample of Release Liner-1 was added on top of the wetted gel coated scrim. The thickness of the saturated gel coated scrim was about 0.5 mm. These samples were packaged in a Foil/Foil Package as described in Comparative Example C1 and allowed to equilibrate for at least seven days prior to testing. Five samples of the gel coated scrim were removed from their packages and tested for Absorbent Capacity (from initial weight) using the Test Method described above using Ringer's solution. The results are shown in Table 1.

Comparative Example C4

Gel coated scrim samples with moisture was prepared as described in Comparative Example C3 except that the packaged sample was gamma irradiated in two passes after packaging at a total dose of 29.5-31.0 kGy (same irradiation as Comparative Example C2) prior to testing its absorbent capacity. Five samples of the gel coated scrim were removed from their packages and tested for Absorbent Capacity (from initial weight) using the Test Method described above using Ringer's solution. The results are shown in Table 1.

Example 1

Gel coated scrim samples with moisture was prepared as described in Comparative Example C3 except that the packaged sample was electron beam irradiated in two passes through the radiation source (80 kW, 5 Mev System) at a totals dose of 31.2-34.5 kGy prior to testing. The dose range for the first pass through the electron beam radiation source was 17.0-19.2 kGy. Five samples of the gel coated scrim were removed from their packages and tested for Absorbent Capacity (from initial weight) using the Test Method described above using Ringer's solution. The results are shown in Table 1.

Comparative Example C5

Samples of 7.5 cm×10 cm gel coated scrim prepared in Comparative Example C1 were placed on a sample of Release Liner-1 and coated with 1.4 grams of sterile water containing 500 ppm PHMB. After adding the sterile water solution, a second sample of Release Liner-1 was added on top of the wetted gel coated scrim. This sample was then packaged in Foil/Foil Packages as described in Example 1 and allowed to equilibrate in the package prior to testing. Five samples of the gel coated scrim were removed from their packages and tested for Absorbent Capacity (from initial weight) using the Test Method described above using Ringer's solution. The results are shown in Table 1.

Comparative Example C6

A gel coated scrim sample with moisture was prepared as described in Comparative Example C5 except that the packaged sample was gamma irradiated after packaging as described in Comparative Example C2. Five samples of the gel coated scrim were removed from their packages and tested for Absorbent Capacity (from initial weight) using the Test Method described above using Ringer's solution. The results are shown in Table 1.

Example 2

A gel coated scrim sample with moisture was prepared as described in Comparative Example C5 except that the packaged sample was electron beam irradiated after packaging as described in Example 1 prior to testing its absorbent capacity. Five samples of the gel coated scrim were removed from their packages and tested for Absorbent Capacity (from initial weight) using the Test Method described above using Ringer's solution. The results are shown in Table 1.

Comparative Example C7

A mixture of 16.9 parts (w/w) Block Copolymer-1, 36.5 parts Mineral Oil with 1% (w/w) Antioxidant-1, 35.6 parts Emulsion-1, and 11 parts CMC were fed, melted, and compounded in a twin screw extruder, and then coated onto the polyester knitted scrim as described in Comparative Example C1. The coating weight of the gel on the scrim was 1.2 grams/24 in$^2$. The gel coated scrim was placed between two sheets of Release Liner-1 with the release side of the liner facing the gel. Samples of 7.5 cm×10 cm pieces of gel coated scrim between liners were cut out, placed in Foil/Foil Packages, and the opening of the package was heat sealed using a bar sealer. Five samples of the gel coated scrim were removed from their packages and tested for Absorbent Capacity (from initial weight) using the Test Method described above using Ringer's solution. The results are shown in Table 1.

Comparative Example C8

Samples of the gel coated scrim in Comparative Example C7 were prepared and packaged as described in Comparative Example C7 except that the packaged samples were gamma irradiated using the same method and dose as that described in Comparative Example C2 prior to testing its absorbent capacity. Five samples of the gel coated scrim were removed from their packages and tested for Absorbent Capacity (from initial weight) using the Test Method described above using Ringer's solution. The results are shown in Table 1.

Comparative Example C9

Samples of 7.5 cm×10 cm gel coated scrim prepared as described in Comparative Example C7 were placed on a sample of Release Liner-1 and coated with 0.7 grams of sterile water containing 500 ppm PHMB. After adding the sterile water solution, a second sample of Release Liner-1 was added on top of the wetted gel coated scrim. These samples were then packaged in Foil/Foil Packages as described in Comparative Example C7 and allowed to equilibrate in the packages prior to testing. Five samples of the gel coated scrim were removed from their packages and tested for Absorbent Capacity (from initial weight) using the Test Method described above using Ringer's solution. The results are shown in Table 1.

Comparative Example C10

A gel coated scrim sample with moisture was prepared as described in Comparative Example C9 except that the packaged sample was gamma irradiated using the dose and method described in Comparative Example C2 prior to testing its absorbent capacity. Five samples of the gel coated scrim were removed from their packages and tested for Absorbent Capacity (from initial weight) using the Test Method described above using Ringer's solution. The results are shown in Table 1.

Example 3

A gel coated scrim sample with moisture was prepared as described in Comparative Example C9 except that the packaged sample was electron beam irradiated using the method and dose described in Example 1 prior to testing its absorbent capacity. Five samples of the gel coated scrim were removed from their packages and tested for Absorbent Capacity (from initial weight) using the Test Method described above using Ringer's solution. The results are shown in Table 1.

Comparative Example C11

7.5 cm×10 cm gel coated scrim samples from Comparative Example C7 were placed on a sample of Release Liner-1 and coated with 1.4 grams of sterile water containing 500 ppm PHMB. After adding the sterile water solution, a second sample of Release Liner-1 was added on top of the wetted gel coated scrim. These samples were packaged in Foil/Foil Packages as described in Comparative Example C7 and allowed to equilibrate in the package. Five samples of the gel coated scrim were removed from their packages and tested for Absorbent Capacity (from initial weight) using the Test Method described above using Ringer's solution. The results are shown in Table 1.

Comparative Example C12

Gel coated scrim samples with moisture was prepared as described in Comparative Example C11 except that the packaged sample was gamma irradiated after packaging using the gamma dose and method described in Comparative Example C2. Five samples of the gel coated scrim were removed from their packages and tested for Absorbent Capacity (from initial weight) using the Test Method described above using Ringer's solution. The results are shown in Table 1.

Example 4

Gel coated scrim samples with moisture was prepared as described in Comparative Example C11 except that the packaged sample was electron beam irradiated after packaging using the dose and method described in Example 1. Five samples of the gel coated scrim were removed from their packages and tested for Absorbent Capacity (from initial weight) using the Test Method described above using Ringer's solution. The results are shown in Table 1.

TABLE 1

| Example | Emulsion-1 Content (wt %) | CMC Content (wt %) | Weight Ratio of Added Water to Dry Gel | E-beam Irradiation Dose (kGy) | Gamma Irradiation Dose (kGy) | Absorbent Capacity (%) |
|---|---|---|---|---|---|---|
| C1 | 39.2 | 1.9 | 0 | None | None | 420 |
| C2 | 39.2 | 1.9 | 0 | None | 29.5-31.0 | 430 |
| C3 | 39.2 | 1.9 | 1.3 | None | None | 211 |
| C4 | 39.2 | 1.9 | 1.3 | None | 29.5-31.0 | 63 |
| 1 | 39.2 | 1.9 | 1.3 | 31.2-34.5 | None | 210 |
| C5 | 39.2 | 1.9 | 2.5 | None | None | 111 |
| C6 | 39.2 | 1.9 | 2.5 | None | 29.5-31.0 | 28 |
| 2 | 39.2 | 1.9 | 2.5 | 31.2-34.5 | None | 113 |
| C7 | 35.6 | 11 | 0 | None | None | 429 |
| C8 | 35.6 | 11 | 0 | None | 29.5-31.0 | 473 |
| C9 | 35.6 | 11 | 1.2 | None | None | 236 |
| C10 | 35.6 | 11 | 1.2 | None | 29.5-31.0 | 81 |
| 3 | 35.6 | 11 | 1.2 | 31.2-34.5 | None | 236 |

TABLE 1-continued

| Example | Emulsion-1 Content (wt %) | CMC Content (wt %) | Weight Ratio of Added Water to Dry Gel | E-beam Irradiation Dose (kGy) | Gamma Irradiation Dose (kGy) | Absorbent Capacity (%) |
|---|---|---|---|---|---|---|
| C11 | 35.6 | 11 | 2.3 | None | None | 130 |
| C12 | 35.6 | 11 | 2.3 | None | 29.5-31.0 | 42 |
| 4 | 35.6 | 11 | 2.3 | 31.2-34.5 | None | 143 |

Examples 5-8 and Comparative Examples C13-C16

Comparative Example C13

A mixture of 18.7 parts (w/w) Block Copolymer-1, 40.2 parts Mineral Oil containing 1% (w/w) Antioxidant-1, 39.2 parts Emulsion-1, and 1.9 parts Cellulose Gum were fed to, melted, and compounded in a twin screw extruder, and then coated on Polyester Scrim as described in Comparative Example C1. The coating weight of the gel on the scrim was 1.2 grams/24 in². The gel coated scrim was placed between two sheets of Release Liner-1 with the release side of the liner facing the gel. A 7.5 cm×10 cm piece of gel coated scrim between liners was cut out, and this piece was placed in a Foil/Foil package and the opening of the package was heat sealed using a bar sealer. This packaged sample was then electron beam irradiated in a single pass at a dose of 29.3-34.0 kGy. The gel coated scrim was removed from the package and separated from the liners, weighed and then placed in approximately 40 grams of an aqueous 0.9% (w/w) sodium chloride solution for two hours to determine its absorbency. The initial weight of the gel coated scrim sample was 1.0 grams. After the absorbency test, the final weight of the sample was 6.3 grams.

Example 5

A 7.5 cm×10 cm gel coated scrim sample prepared as described in Comparative Example C13 was placed on a sample of Release Liner-1 and then coated with approximately 2 grams of sterile water containing 500 ppm PHMB. After adding the sterile water solution, a second sample of Release Liner-1 was added on top of the wetted gel coated scrim. This sample was packaged in a Foil/Foil Package and allowed to equilibrate. The sample was electron beam irradiated as described in Comparative Example C13. The initial weight of the sample prior to absorbency testing was 3.0 grams. After the absorbent test in an aqueous 0.9% (w/w) sodium chloride solution for two hours, the weight of the sample was 5.1 grams.

Comparative Example C14

The procedure described for Comparative Example C13 was followed, except that the absorbency test was conducted in sterile water instead of an aqueous 0.9% sodium chloride solution. The weight of the sample prior to absorbent testing was 1.2 grams. The weight of the sample after absorbency testing in sterile water for two hours was 27.8 grams.

Example 6

A 7.5 cm×10 cm gel coated scrim sample from Comparative Example C13 was placed on a sample of Release Liner-1 and then coated with approximately 2.2 grams of sterile water containing 500 ppm PHMB. After adding the sterile water solution, a second sample of Release Liner-1 was added on top of the wetted gel coated scrim. This sample was packaged in a Foil/Foil Package and electron beam irradiated as described in Comparative Example C13. The initial weight of the sample prior to absorbency testing was 3.3 grams. After the absorbency test in sterile water for 2 hours, the weight of the sample was 28.2 grams.

Comparative Example C15

A mixture of 16.9 parts (w/w) Block Copolymer-1, 36.5 parts Mineral Oil containing 1% (w/w) Antioxidant-1, 35.6 parts Emulsion-1, and 11 parts Cellulose Gum were fed to, melted, and compounded in a twin screw extruder, and then coated on Polyester Scrim as described in Comparative Example C1. The coating weight of the gel on the scrim was 1.2 grams/24 in². The gel coated scrim was placed between two sheets of Release Liner-1 with the release side of the liner facing the gel. A 7.5 cm×10 cm piece of gel coated scrim between liners was cut out, and this piece was placed in a Foil/Foil Package and the opening of the package was heat sealed using a bar sealer. This packaged sample was electron beam irradiated in a single pass at a dose of 29.3-34.0 kGy. The gel coated scrim was removed from the package and separated from the liners, weighed and then placed in approximately 40 grams of an aqueous 0.9% (w/w) sodium chloride solution for 2 hours to determine its absorbent capacity. The initial weight of the gel coated scrim sample was 1.2 grams. After the absorbency test, the final weight of the sample was 7.2 grams.

Example 7

A 7.5 cm×10 cm gel coated scrim sample prepared as described in Comparative Example C15 was placed on a sample of Release Liner-1 and then coated with approximately 2 grams of sterile water containing 500 ppm PHMB. After adding the sterile water solution, a second sample of Release Liner-1 was added on top of the wetted gel coated scrim. This sample was then packaged in a Foil/Foil Package, allowed to equilibrate, and electron beam irradiated as described in Comparative Example C15. The initial weight of the sample was 2.9 grams. After the absorbency test in the aqueous 0.9% (w/w) sodium chloride solution, the weight of the sample was 7.5 grams.

Comparative Example C16

The procedure described for Comparative Example C15 was followed, except that the absorbency test was conducted in sterile water instead of an aqueous 0.9% sodium chloride solution. The weight of the sample prior to absorbency testing was 1.0 grams. The weight of the sample after absorbency testing in sterile water was 26.9 grams.

Example 8

A 7.5 cm×10 cm gel coated scrim sample prepared as described in Comparative Example C15 was placed on a sample of Release Liner-1 and then coated with approximately 1.8 grams of sterile water containing 500 ppm PHMB. After adding the sterile water solution, a second sample of Release Liner-1 was added on top of the wetted gel coated scrim. This sample was then packaged in a Foil/Foil Package, allowed to equilibrate, and electron beam irradiated as described in Comparative Example C15. The initial weight of the sample prior to absorbency testing was 2.7 grams. After the absorbency test in sterile water for 2 hours, the weight of the sample was 25.9 grams.

their packages and tested for Absorbent Capacity (from initial dry weight) using the Test Method described above using Ringer's solution. The results are shown in Table 3.

Comparative Example C20

Samples of 5 cm×10 cm pieces of the gel coated scrim from Comparative Example C17 (before packaging) were placed on samples of Release Liner-1 and coated with about 0.1 grams of sterile water containing 500 ppm PHMB. After

TABLE 2

| Example | Emulsion-1 Content (wt %) | Cellulose Gum Content (wt %) | Weight Ratio of Added Water to Dry Gel | Absorbency Test Solution | Weight of sample prior to 2 hour absorbency test (grams) | Weight of sample after 2 hour absorbency test (grams) |
|---|---|---|---|---|---|---|
| C13 | 39.2 | 1.9 | 0 | 0.9% NaCl | 1.0 | 6.3 |
| 5 | 39.2 | 1.9 | ~3.3 | 0.9% NaCl | 3.0 | 5.1 |
| C14 | 39.2 | 1.9 | 0 | Sterile water | 1.2 | 27.8 |
| 6 | 39.2 | 1.9 | ~3.7 | Sterile water | 3.3 | 28.2 |
| C15 | 35.6 | 11 | 0 | 0.9% NaCl | 1.2 | 7.2 |
| 7 | 35.6 | 11 | ~3.3 | 0.9% NaCl | 2.9 | 7.5 |
| C16 | 35.6 | 11 | 0 | Sterile water | 1.0 | 26.9 |
| 8 | 35.6 | 11 | ~3.0 | Sterile water | 2.7 | 25.9 |

Examples 9-24 and Comparative Examples C17-C45

Comparative Example C17

A gel coated scrim was prepared like that described in Comparative Example C1 except the gel was comprised of a mixture of approximately 18 parts (w/w) Block Copolymer-1, 42 parts Mineral Oil containing 1% (w/w) Antioxidant-1, 38 parts Emulsion-1, and 2 parts CMC powder. The coating weight of the gel on the scrim ranged from about 1.3 to 1.5 grams/24 in². The thickness of the gel coated scrim was about 0.5 mm. The gel coated scrim was placed between two sheets of Release Liner-1 with the release side of the liner facing the gel. 5 cm×10 cm pieces of gel coated scrim between liners was cut out, and the pieces were placed in a Foil/Foil Package and the opening of the package was heat sealed using a bar sealer prior to measuring its absorbent properties. Four samples of the gel coated scrim were removed from their packages and tested for Absorbent Capacity (from initial dry weight) using the Test Method described above using Ringer's solution. The results are shown in Table 3.

Comparative Example C18

Gel coated scrim samples were prepared and packaged as described in Comparative Example C17. The packaged samples were then gamma irradiated using a Cobalt-60 source at 29.5-34.0 kGy. Four samples of the gel coated scrim were removed from their packages and tested for Absorbent Capacity (from initial dry weight) using the Test Method described above using Ringer's solution. The results are shown in Table 3.

Comparative Example C19

Gel coated scrim samples were prepared and packaged as described in Comparative Example C17. The packaged sample was then electron beam irradiated using a 80 kW, 5 Mev system at a total dose of 35.6-39.2 kGy prior to testing. Four samples of the gel coated scrim were removed from adding the sterile water solution, a second sample of Release Liner-1 was added on top of the wetted gel coated scrim. The thickness of the saturated gel coated scrim was about 0.5 mm. These samples were then packaged in a Foil/Foil Package as described in Comparative Example C17 and allowed to equilibrate for at least seven days prior to testing. Four samples of the gel coated scrim were removed from their packages and tested for Absorbent Capacity (from initial dry weight) using the Test Method described above using Ringer's solution. The results are shown in Table 3.

Example 9

Samples of gel coated scrim were prepared and packaged as described in Comparative Example C20. The packaged, equilibrated sample was then gamma irradiated using a Cobalt-60 source at 29.5-34.0 kGy. Four samples of the gel coated scrim were removed from their packages and tested for Absorbent Capacity (from initial dry weight) using the Test Method described above using Ringer's solution. The results are shown in Table 3.

Example 10

Samples of gel coated scrim were prepared and packaged as described in Comparative Example C20. The packaged, equilibrated sample was then electron beam irradiated using a 80 kW, 5 Mev system at a totals dose of 35.6-39.2 kGy. Four samples of the gel coated scrim were removed from their packages and tested for Absorbent Capacity (from initial dry weight) using the Test Method described above using Ringer's solution. The results are shown in Table 3.

Comparative Example C21

Samples of gel coated scrim were prepared and packaged as described in Comparative Example C20 except about 0.4 grams of sterile water containing 500 ppm PHMB was coated onto the gel coated scrim. Four samples of the gel coated scrim were removed from their packages and tested for Absorbent Capacity (from initial dry weight) using the Test Method described above using Ringer's solution. The results are shown in Table 3.

Example 11

Samples of gel coated scrim were prepared and packaged as described in Comparative Example C21. The packaged, equilibrated sample was then gamma irradiated using a Cobalt-60 source at 29.5-34.0 kGy. Four samples of the gel coated scrim were removed from their packages and tested for Absorbent Capacity (from initial dry weight) using the Test Method described above using Ringer's solution. The results are shown in Table 3.

Example 12

Samples of gel coated scrim were prepared and packaged as described in Comparative Example C21. The packaged, equilibrated sample was then electron beam irradiated using a 80 kW, 5 Mev system at a totals dose of 35.6-39.2 kGy. Four samples of the gel coated scrim were removed from their packages and tested for Absorbent Capacity (from initial dry weight) using the Test Method described above using Ringer's solution. The results are shown in Table 3.

Comparative Example C22

Samples of gel coated scrim were prepared and packaged as described in Comparative Example C20 except about 0.85 grams of sterile water containing 500 ppm PHMB was coated onto the gel coated scrim. Four samples of the gel coated scrim were removed from their packages and tested for Absorbent Capacity (from initial dry weight) using the Test Method described above using Ringer's solution. The results are shown in Table 3.

Comparative Example C23

Samples of gel coated scrim were prepared and packaged as described in Comparative Example C22. The packaged, equilibrated sample was then gamma irradiated using a Cobalt-60 source at 29.5-34.0 kGy. Four samples of the gel coated scrim were removed from their packages and tested for Absorbent Capacity (from initial dry weight) using the Test Method described above using Ringer's solution. The results are shown in Table 3.

Example 13

Samples of gel coated scrim were prepared and packaged as described in Comparative Example C22. The packaged, equilibrated sample was then electron beam irradiated using a 80 kW, 5 Mev system at a totals dose of 35.6-39.2 kGy. Four samples of the gel coated scrim were removed from their packages and tested for Absorbent Capacity (from initial dry weight) using the Test Method described above using Ringer's solution. The results are shown in Table 3.

Comparative Example C24

Samples of gel coated scrim were prepared and packaged as described in Comparative Example C20 except about 2.1 grams of sterile water containing 500 ppm PHMB was coated onto the gel coated scrim. Four samples of the gel coated scrim were removed from their packages and tested for Absorbent Capacity (from initial dry weight) using the Test Method described above using Ringer's solution. The results are shown in Table 3.

Example 14

Samples of gel coated scrim were prepared and packaged as described in Comparative Example C24. The packaged, equilibrated sample was electron beam irradiated using a 80 kW, 5 Mev system at a totals dose of 35.6-39.2 kGy. Four samples of the gel coated scrim were removed from their packages and tested for Absorbent Capacity (from initial dry weight) using the Test Method described above using Ringer's solution. The results are shown in Table 3.

Comparative Example C25

Samples of gel coated scrim were prepared and packaged as described in Comparative Example C20 except about 3.4 grams of sterile water containing 500 ppm PHMB was coated onto the gel coated scrim. Four samples of the gel coated scrim were removed from their packages and tested for Absorbent Capacity (from initial dry weight) using the Test Method described above using Ringer's solution. The results are shown in Table 3.

Example 15

Samples of gel coated scrim were prepared and packaged as described in Comparative Example C25. The packaged, equilibrated sample was then electron beam irradiated using a 80 kW, 5 Mev system at a totals dose of 35.6-39.2 kGy. Four samples of the gel coated scrim were removed from their packages and tested for Absorbent Capacity (from initial dry weight) using the Test Method described above using Ringer's solution. The results are shown in Table 3.

Comparative Example C26

A gel coated scrim was prepared like that described in Comparative Example C1 except the gel was comprised of a mixture of approximately 18 parts (w/w) Block Copolymer-1, 42 parts Mineral Oil containing 1% (w/w) Antioxidant-1, and 38 parts Emulsion-1. The coating weight of the gel on the scrim ranged from about 1.2 to 1.3 grams/24 in$^2$. The thickness of the gel coated scrim was about 0.5 mm. The gel coated scrim was placed between two sheets of Release Liner-1 with the release side of the liner facing the gel. Samples of 5 cm×10 cm pieces of gel coated scrim between liners were cut out, and the pieces were placed in Foil/Foil packages and the opening of the package was heat sealed using a bar sealer. Four samples of the gel coated scrim were removed from their packages and tested for Absorbent Capacity (from initial dry weight) using the Test Method described above using Ringer's solution. The results are shown in Table 3.

Comparative Example C27

Samples of gel coated scrim were prepared and packaged as described in Comparative Example C26. The packaged sample was then gamma irradiated using a Cobalt-60 source at 29.5-34.0 kGy. Four samples of the gel coated scrim were removed from their packages and tested for Absorbent Capacity (from initial dry weight) using the Test Method described above using Ringer's solution. The results are shown in Table 3.

Comparative Example C28

Samples of gel coated scrim were prepared and packaged as described in Comparative Example C26. The packaged sample was then electron beam irradiated using a 80 kW, 5 Mev system at a totals dose of 35.6-39.2 kGy. Four samples of the gel coated scrim were removed from their packages and tested for Absorbent Capacity (from initial dry weight) using the Test Method described above using Ringer's solution. The results are shown in Table 3.

Comparative Example C29

Samples of 5 cm×10 cm gel coated scrim were prepared as described in Comparative Example C26 and placed on a sample of Release Liner-1 and then coated with approximately 0.1 gram of sterile water containing 500 ppm PHMB. After adding the sterile water solution, a second sample of Release Liner-1 was added on top of the wetted gel coated scrim. The thickness of the saturated gel coated scrim was about 0.5 mm. These samples were then packaged in Foil/Foil Packages, allowed to equilibrate for at least seven days prior to testing. Four samples of the gel coated scrim were removed from their packages and tested for Absorbent Capacity (from initial dry weight) using the Test Method described above using Ringer's solution. The results are shown in Table 3.

Example 16

Samples of gel coated scrim were prepared and packaged as described in Comparative Example C29. The packaged, equilibrated sample was then gamma irradiated using a Cobalt-60 source at 29.5-34.0 kGy. Four samples of the gel coated scrim were removed from their packages and tested for Absorbent Capacity (from initial dry weight) using the Test Method described above using Ringer's solution. The results are shown in Table 3.

Example 17

Samples of gel coated scrim were prepared and packaged as described in Comparative Example C29. The packaged sample was then electron beam irradiated using a 80 kW, 5 Mev system at a totals dose of 35.6-39.2 kGy prior to testing. Four samples of the gel coated scrim were removed from their packages and tested for Absorbent Capacity (from initial dry weight) using the Test Method described above using Ringer's solution. The results are shown in Table 3.

Comparative Example C30

Samples of gel coated scrim were prepared and packaged as described in Comparative Example C29 except about 0.42 grams of sterile water containing 500 ppm PHMB was coated onto the gel coated scrim. Four samples of the gel coated scrim were removed from their packages and tested for Absorbent Capacity (from initial dry weight) using the Test Method described above using Ringer's solution. The results are shown in Table 3.

Comparative Example C31

Samples of gel coated scrim were prepared and packaged as described in Comparative Example C30. The packaged, equilibrated sample was then gamma irradiated using a Cobalt-60 source at 29.5-34.0 kGy. Four samples of the gel coated scrim were removed from their packages and tested for Absorbent Capacity (from initial dry weight) using the Test Method described above using Ringer's solution. The results are shown in Table 3.

Example 18

Samples of gel coated scrim were prepared and packaged as described in Comparative Example C30. The packaged, equilibrated sample was then electron beam irradiated using a 80 kW, 5 Mev system at a totals dose of 35.6-39.2 kGy. Four samples of the gel coated scrim were removed from their packages and tested for Absorbent Capacity (from initial dry weight) using the Test Method described above using Ringer's solution. The results are shown in Table 3.

Comparative Example C32

Samples of gel coated scrim were prepared and packaged as described in Comparative Example C29 except about 0.85 grams of sterile water containing 500 ppm PHMB was coated onto the gel coated scrim. Four samples of the gel coated scrim were removed from their packages and tested for Absorbent Capacity (from initial dry weight) using the Test Method described above using Ringer's solution. The results are shown in Table 3.

Example 19

Samples of gel coated scrim were prepared and packaged as described in Comparative Example C32. The packaged, equilibrated sample was then electron beam irradiated using a 80 kW, 5 Mev system at a totals dose of 35.6-39.2 kGy. Four samples of the gel coated scrim were removed from their packages and tested for Absorbent Capacity (from initial dry weight) using the Test Method described above using Ringer's solution. The results are shown in Table 3.

Comparative Example C33

Samples of gel coated scrim were prepared and packaged as described in Comparative Example C29 except about 2.1 grams of sterile water containing 500 ppm PHMB was coated onto the gel coated scrim. Four samples of the gel coated scrim were removed from their packages and tested for Absorbent Capacity (from initial dry weight) using the Test Method described above using Ringer's solution. The results are shown in Table 3.

Example 20

Samples of gel coated scrim were prepared and packaged as described in Comparative Example C33. The packaged, equilibrated sample was then electron beam irradiated using a 80 kW, 5 Mev system at a totals dose of 35.6-39.2 kGy. Four samples of the gel coated scrim were removed from their packages and tested for Absorbent Capacity (from initial dry weight) using the Test Method described above using Ringer's solution. The results are shown in Table 3.

Comparative Example C34

A gel coated scrim was prepared like that described in Comparative Example C1 except the gel was comprised of a mixture of approximately 18 parts (w/w) Block Copolymer-1, 42 parts Mineral Oil containing 1% (w/w) Antioxidant-1, and 38 parts Emulsion-2. The coating weight of the gel on the scrim ranged from about 1.1 grams/24 in². The thickness of the gel coated scrim was about 0.5 mm. The gel coated scrim was placed between two sheets of Release Liner-1 with the release side of the liner facing the gel. Samples of 5 cm×10 cm pieces of gel coated scrim between liners were cut out, and the pieces were placed in Foil/Foil packages and the opening of the package was heat sealed using a bar sealer. Four samples of the gel coated scrim were removed from their packages and tested for Absorbent Capacity (from initial dry weight) using the Test Method described above using Ringer's solution. The results are shown in Table 3.

Comparative Example C35

Samples of gel coated scrim were prepared and packaged as described in Comparative Example C34. The packaged sample was then electron beam irradiated using a 80 kW, 5 Mev system at a totals dose of 35.6-39.2 kGy. Four samples of the gel coated scrim were removed from their packages and tested for Absorbent Capacity (from initial dry weight) using the Test Method described above using Ringer's solution. The results are shown in Table 3.

Comparative Example C36

Samples of 5 cm×10 cm gel coated scrim were prepared as described in Comparative Example C34 and placed on a sample of Release Liner-1 and then coated with approximately 0.42 gram of sterile water containing 500 ppm PHMB. After adding the sterile water solution, a second sample of Release Liner-1 was added on top of the wetted gel coated scrim. The thickness of the saturated gel coated scrim was about 0.5 mm. These samples were then packaged in Foil/Foil Packages, allowed to equilibrate for at least seven days prior to testing. Four samples of the gel coated scrim were removed from their packages and tested for Absorbent Capacity (from initial dry weight) using the Test Method described above using Ringer's solution. The results are shown in Table 3.

Comparative Example C37

Samples of gel coated scrim were prepared and packaged as described in Comparative Example C36. The packaged sample was then electron beam irradiated using a 80 kW, 5 Mev system at a totals dose of 35.6-39.2 kGy. Four samples of the gel coated scrim were removed from their packages and tested for Absorbent Capacity (from initial dry weight) using the Test Method described above using Ringer's solution. The results are shown in Table 3.

Comparative Example C38

Samples of gel coated scrim were prepared and packaged as described in Comparative Example C20 except about 0.4 grams of sterile water was coated onto the gel coated scrim. Four samples of the gel coated scrim were removed from their packages and tested for Absorbent Capacity (from initial dry weight) using the Test Method described above using Ringer's solution. The results are shown in Table 3.

Example 21

Samples of gel coated scrim were prepared and packaged as described in Comparative Example C38. The packaged, equilibrated sample was then gamma irradiated using a Cobalt-60 source at 35.4-38.0 kGy. Four samples of the gel coated scrim were removed from their packages and tested for Absorbent Capacity (from initial dry weight) using the Test Method described above using Ringer's solution. The results are shown in Table 3.

Example 22

Samples of gel coated scrim were prepared and packaged as described in Comparative Example C38. The packaged, equilibrated sample was then electron beam irradiated using a 80 kW, 5 Mev system at a totals dose of 34.3-38.4 kGy. Four samples of the gel coated scrim were removed from their packages and tested for Absorbent Capacity (from initial dry weight) using the Test Method described above using Ringer's solution. The results are shown in Table 3.

Comparative Example C39

Samples of gel coated scrim were prepared and packaged as described in Comparative Example C20 except about 0.85 grams of sterile water was coated onto the gel coated scrim. Four samples of the gel coated scrim were removed from their packages and tested for Absorbent Capacity (from initial dry weight) using the Test Method described above using Ringer's solution. The results are shown in Table 3.

Comparative Example C40

Samples of gel coated scrim were prepared and packaged as described in Comparative Example C39. The packaged, equilibrated sample was then gamma irradiated using a Cobalt-60 source at 35.4-38.0 kGy. Four samples of the gel coated scrim were removed from their packages and tested for Absorbent Capacity (from initial dry weight) using the Test Method described above using Ringer's solution. The results are shown in Table 3.

Example 23

Samples of gel coated scrim were prepared and packaged as described in Comparative Example C39. The packaged, equilibrated sample was then electron beam irradiated using a 80 kW, 5 Mev system at a totals dose of 34.3-38.4 kGy. Four samples of the gel coated scrim were removed from their packages and tested for Absorbent Capacity (from initial dry weight) using the Test Method described above using Ringer's solution. The results are shown in Table 3.

Comparative Example C41

Samples of gel coated scrim were prepared and packaged as described in Comparative Example C29 except about 0.85 grams of sterile water was coated onto the gel coated scrim. Four samples of the gel coated scrim were removed from their packages and tested for Absorbent Capacity (from initial dry weight) using the Test Method described above using Ringer's solution. The results are shown in Table 3.

Comparative Example C42

Samples of gel coated scrim were prepared and packaged as described in Comparative Example C41. The packaged, equilibrated sample was then gamma irradiated using a Cobalt-60 source at 35.4-38.0 kGy. Four samples of the gel coated scrim were removed from their packages and tested for Absorbent Capacity (from initial dry weight) using the Test Method described above using Ringer's solution. The results are shown in Table 3.

Example 24

Samples of gel coated scrim were prepared and packaged as described in Comparative Example C41. The packaged, equilibrated sample was then electron beam irradiated using a 80 kW, 5 Mev system at a totals dose of 34.3-38.4 kGy. Four samples of the gel coated scrim were removed from their packages and tested for Absorbent Capacity (from initial dry weight) using the Test Method described above using Ringer's solution. The results are shown in Table 3.

Comparative Example C43

Samples of gel coated scrim were prepared and packaged as described in Comparative Example C36 except about 0.40 grams of sterile water was coated onto the gel coated scrim. Four samples of the gel coated scrim were removed from their packages and tested for Absorbent Capacity (from initial dry weight) using the Test Method described above using Ringer's solution. The results are shown in Table 3.

Comparative Example C44

Samples of gel coated scrim were prepared and packaged as described in Comparative Example C43. The packaged, equilibrated sample was then gamma irradiated using a Cobalt-60 source at 35.4-38.0 kGy. Four samples of the gel coated scrim were removed from their packages and tested for Absorbent Capacity (from initial dry weight) using the Test Method described above using Ringer's solution. The results are shown in Table 3.

Comparative Example C45

Samples of gel coated scrim were prepared and packaged as described in Comparative Example C43. The packaged, equilibrated sample was then electron beam irradiated using a 80 kW, 5 Mev system at a totals dose of 34.3-38.4 kGy. Four samples of the gel coated scrim were removed from their packages and tested for Absorbent Capacity (from initial dry weight) using the Test Method described above using Ringer's solution. The results are shown in Table 3.

TABLE 3

| Example | Emulsion-1 Content (wt %) | Emulsion-2 Content (wt %) | CMC Content (wt %) | Weight Ratio of Added Water to Dry Gel | E-beam Irradiation Dose (kGy) | Gamma Irradiation Dose (kGy) | Absorbent Capacity (%) |
|---|---|---|---|---|---|---|---|
| C17 | 38 | 0 | 2 | 0 | None | None | 540 |
| C18 | 38 | 0 | 2 | 0 | None | 29.5-34.0 | 490 |
| C19 | 38 | 0 | 2 | 0 | 35.6-39.2 | None | 460 |
| C20 | 38 | 0 | 2 | 0.2 | None | None | 440 |
| 9 | 38 | 0 | 2 | 0.2 | None | 29.5-34.0 | 430 |
| 10 | 38 | 0 | 2 | 0.2 | 35.6-39.2 | None | 350 |
| C21 | 38 | 0 | 2 | 0.85 | None | None | 470 |
| 11 | 38 | 0 | 2 | 0.85 | None | 29.5-34.0 | 340 |
| 12 | 38 | 0 | 2 | 0.85 | 35.6-39.2 | None | 420 |
| C22 | 38 | 0 | 2 | 1.8 | None | None | 460 |
| C23 | 38 | 0 | 2 | 1.8 | None | 29.5-34.0 | 180 |
| 13 | 38 | 0 | 2 | 1.8 | 35.6-39.2 | None | 440 |
| C24 | 38 | 0 | 2 | 4.3 | None | None | 520 |
| 14 | 38 | 0 | 2 | 4.3 | 35.6-39.2 | None | 460 |
| C25 | 38 | 0 | 2 | 6.8 | None | None | 600 |
| 15 | 38 | 0 | 2 | 6.8 | 35.6-39.2 | None | 310 |
| C26 | 38 | 0 | 0 | 0 | None | None | 490 |
| C27 | 38 | 0 | 0 | 0 | None | 29.5-34.0 | 420 |
| C28 | 38 | 0 | 0 | 0 | 35.6-39.2 | None | 410 |
| C29 | 38 | 0 | 0 | 0.2 | None | None | 480 |
| 16 | 38 | 0 | 0 | 0.2 | None | 29.5-34.0 | 400 |
| 17 | 38 | 0 | 0 | 0.2 | 35.6-39.2 | None | 340 |
| C30 | 38 | 0 | 0 | 0.85 | None | None | 540 |
| C31 | 38 | 0 | 0 | 0.85 | None | 29.5-34.0 | 200 |
| 18 | 38 | 0 | 0 | 0.85 | 35.6-39.2 | None | 420 |
| C32 | 38 | 0 | 0 | 2.0 | None | None | 540 |
| 19 | 38 | 0 | 0 | 2.0 | 35.6-39.2 | None | 410 |
| C33 | 38 | 0 | 0 | 4.9 | None | None | 520 |
| 20 | 38 | 0 | 0 | 4.9 | 35.6-39.2 | None | 320 |
| C34 | 0 | 38 | 0 | 0 | None | None | 310 |
| C35 | 0 | 38 | 0 | 0 | 35.6-39.2 | None | 310 |
| C36 | 0 | 38 | 0 | 1.3 | None | None | 340 |
| C37 | 0 | 38 | 0 | 1.3 | 35.6-39.2 | None | 150 |
| C38 | 38 | 0 | 2 | 0.8 | None | None | 360 |
| 21 | 38 | 0 | 2 | 0.8 | None | 35.4-38.0 | 230 |
| 22 | 38 | 0 | 2 | 0.8 | 34.3-38.4 | None | 360 |
| C39 | 38 | 0 | 2 | 1.7 | None | None | 410 |
| C40 | 38 | 0 | 2 | 1.7 | None | 35.4-38.0 | 100 |
| 23 | 38 | 0 | 2 | 1.7 | 34.3-38.4 | None | 400 |
| C41 | 38 | 0 | 0 | 2.0 | None | None | 350 |
| C42 | 38 | 0 | 0 | 2.0 | None | 35.4-38.0 | 90 |
| 24 | 38 | 0 | 0 | 2.0 | 34.3-38.4 | None | 340 |
| C43 | 0 | 38 | 0 | 1.2 | None | None | 240 |
| C44 | 0 | 38 | 0 | 1.2 | None | 35.4-38.0 | 60 |
| C45 | 0 | 38 | 0 | 1.2 | 34.3-38.4 | None | 80 |

What is claimed is:

1. A method of sterilizing an article comprising:
providing an article wherein the article comprises:
a polymer layer, wherein the polymer layer comprises:
a hydrophobic organic matrix comprising:
an elastomeric polymer; and
hydrophilic polymeric microparticles dispersed within the elastomeric polymer;
applying an aqueous solution to the polymer layer to at least partially swell the hydrophilic microparticles; and
subsequently applying electron beam radiation to the article to effect sterilization without degrading or crosslinking the hydrophilic polymeric microparticles.

2. The method of claim 1, further comprising placing the article into a non-porous package after applying an aqueous solution and prior to applying electron beam radiation.

3. The method of claim 1, wherein the polymer layer further comprises hydrophilic particles of greater than 10 micrometer average particle size.

4. The method of claim 1, wherein the elastomeric polymer comprises a styrene block copolymer.

5. The method of claim 1, wherein the hydrophilic microparticles comprise crosslinked acrylic microparticles.

6. The method of claim 1, wherein the microparticles are present in an amount of 1 wt-% to 60 wt-%, based on the total weight of the layer.

7. The method of claim 1, wherein the polymer layer further comprises a porous web.

8. The method of claim 1, wherein the article further comprises a protective liner.

9. The method of claim 1, wherein the application of an aqueous solution comprises a weight ratio of the weight of applied aqueous solution to the weight of microparticles of from 0.2:1 to 30:1.

10. The method of claim 1, wherein applying electron beam radiation comprises a minimum cumulative dose of 15 kGy.

11. The method of claim 1, wherein the absorbent capacity, as measured by the Absorbent Capacity Test Method, of the article after application of the electron beam radiation is at least 60% of the absorbent capacity prior to application of the electron beam radiation.

12. The method of claim 1, wherein the density of the article after the application of an aqueous solution is in the range of 0.8 to 1.2 grams per cubic centimeter.

13. The method of claim 1, wherein the article comprises a porous article.

14. The method of claim 13, wherein the density of the porous article is in the range of 0.10 to 0.9 grams per cubic centimeter.

15. The method of claim 1, wherein the thickness of the layer after the application of the aqueous solution is less than 5 millimeters.

16. The method of claim 1, wherein applying electron beam radiation to the article comprises exposure of the article to electron beam radiation for less than 5 minutes of exposure time.

17. A method of sterilizing an article comprising:
providing an article, wherein the article comprises:
a polymer layer, wherein the polymer layer comprises:
a hydrophobic organic matrix comprising:
an elastomeric polymer;
hydrophilic polymeric microparticles dispersed within the hydrophobic organic matrix; and
hydrophilic polymer particles with greater than 10 micrometers average particle size dispersed within the hydrophobic organic matrix;
applying an aqueous solution to the polymer layer such that the ratio of water to hydrophilic polymeric microparticles is in the range of 0.2:1 to 6:1 to at least partially swell the hydrophilic microparticles; and
subsequently applying gamma radiation to the article to effect sterilization without degrading or crosslinking the hydrophilic polymeric microparticles.

18. The method of claim 17, further comprising placing the article into a non-porous package after applying an aqueous solution and prior to applying gamma radiation.

19. The method of claim 17, wherein the hydrophilic particles of greater than 10 micrometer average particle size comprise carboxymethyl cellulose.

20. The method of claim 17, wherein the elastomeric polymer comprises a styrene block copolymer.

* * * * *

UNITED STATES PATENT AND TRADEMARK OFFICE
CERTIFICATE OF CORRECTION

PATENT NO.        : 9,439,809 B2
APPLICATION NO.   : 13/635536
DATED             : September 13, 2016
INVENTOR(S)       : David Holm It is certified that error appears in the above-identified patent and that said Letters Patent is hereby corrected as shown below:

On the Title Page

Column 2 (Other Publications)
Line 12, Delete "Rersearch" and insert -- Research --, therefor.

In the Specification

Column 3
Line 59, Delete "that" and insert -- than --, therefor.

Column 6
Line 15, Delete "diisoctyl" and insert -- diisooctyl --, therefor.

Column 7
Line 40, Delete "lineomycin," and insert -- lincomycin, --, therefor.
Line 50, Delete "lineomycin," and insert -- lincomycin, --, therefor.
Line 56, Delete "ketaconazole," and insert -- ketoconazole, --, therefor.
Line 56, Delete "amanfadine" and insert -- amantadine --, therefor.
Line 56, Delete "amanfadine" and insert -- amantadine --, therefor.

Column 8
Line 2, Delete "thimersal" and insert -- thimerosal --, therefor.
Line 2, Delete "chlorphenenesin," and insert -- chlorphenesin, --, therefor.
Line 14, Delete "pchlorophenol" and insert -- p-chlorophenol --, therefor.
Line 18, Delete "ochlorophenol," and insert -- o-chlorophenol, --, therefor.
Line 28, Delete "pchlorophenol" and insert -- p-chlorophenol --, therefor.
Line 33, Delete "pbromophenol," and insert -- p-bromophenol, --, therefor.

Signed and Sealed this
Fifth Day of September, 2017

Joseph Matal
*Performing the Functions and Duties of the*
*Under Secretary of Commerce for Intellectual Property and*
*Director of the United States Patent and Trademark Office*

Column 9
Line 8-9, Delete "Hydastis carradensis," and insert -- Hydrastis canadensis, --, therefor.
Line 17, Delete "carvacol," and insert -- carvacrol, --, therefor.
Line 18, Delete "caryophellene" and insert -- caryophyllene --, therefor.

Column 10
Line 40, Delete "polysaccarides" and insert -- polysaccharides --, therefor.
Line 44, Delete "Furcelleran" and insert -- Furcellaran --, therefor.
Line 49, Delete "-hydroxpropyl)" and insert -- -hydroxypropyl) --, therefor.
Line 52, Delete "-hydroxylpropyllmethacrylamide," and insert
-- -hydroxypropylmethacrylamide, --, therefor.
Line 53-54, Delete "-oxabutyllacrylamide));" and insert -- -oxabutylacrylamide)); --, therefor.

Column 18
Line 45, Delete "from" and insert -- form --, therefor.

Column 21
Line 22, Delete "coomercially" and insert -- commercially --, therefor.
Line 27, Delete "biquanide," and insert -- biguanide, --, therefor.